(12) United States Patent
Reppert et al.

(10) Patent No.: US 6,326,526 B1
(45) Date of Patent: Dec. 4, 2001

(54) MELATONIN RECEPTOR-DEFICIENT MICE AND USES THEREOF

(75) Inventors: Steven M. Reppert, Newtown, MA (US); Valentin K. Gribkoff, Wallingford, CT (US)

(73) Assignees: Bristol-Myers Squibb Company, Princeton, NJ (US); The General Hospital Corporation, Boston, MA (US)

(*) Notice: Subject to any disclaimer, the term of this patent is extended or adjusted under 35 U.S.C. 154(b) by 0 days.

(21) Appl. No.: 09/479,195

(22) Filed: Jan. 7, 2000

Related U.S. Application Data

(62) Division of application No. 09/122,527, filed on Jul. 24, 1998, now abandoned.
(60) Provisional application No. 60/053,565, filed on Jul. 24, 1997.

(51) Int. Cl.[7] .................. A01K 67/027; A01K 67/00; G01N 33/00; C12P 21/06; C12N 15/09
(52) U.S. Cl. .................... 800/18; 800/3; 800/13; 435/69.1; 435/69.2; 435/325
(58) Field of Search .................. 800/13, 8, 3, 4; 435/325; 536/23.5

(56) References Cited

PUBLICATIONS

Campbell et al. Theriogenology 47(1):63–72 Jan. 1997.*
Capecchi M.R. Science 244:1288–1292 Jun. 1989.*
Arendt et al., Some effects of jet–lag and their alleviation by melatonin, Ergonomics 30:1379–1393 (1987).
Benloucif et al., Melatonin and light induce phase shifts of circadian rhythms in the C3H/HeN mouse, J. Biol. Rythms 11:113–125 (1996).
Bouskila et al., Neuronal synchronization without calcium–dependent synaptic transmission in the hypothalamus Proc. Natl. Acad. Sci. USA 90:3207–3210 (1993).
Bouskila et al., A rapidly activating type of outward rectifier K+ current and A–current in rat suprachiasmatic nucleus neurones. J. Physiol. 488:339–350 (1995).
Bradley, In Teratocarcinomas and Embryonic Stem Cells, E.J. Robertson, ed. (Oxford, England:IRL Press), pp. 113–151 (1987).
Davis et al., Entrainment of hamster pup circadian rhythms by prenatal melatonin injections to the mother, Am. J. Physiol. 255:R439–R448 (1988).
Ding et al., Resetting the biological clock: mediation of nocturnal circadian shifts by glutamate and No, Science 266:1713–1717 (1994).
Dubocovich et al., Melatonin receptors in the mammalian suprachiasmatic nucleus. Behav. Brain Res. 73:141–147 (1995).

Duncan et al., Developmental appearance and age related changes in specific 2–[$^{125}$I]iodomelatonin binding sites in the suprachiasmatic nuclei of female Syrian hamsters. Dev. Brain Res. 73:205–212 (1993).
Goto et al., Melatonin content of the pineal gland in different mouse strains, J. Pineal Res. 7:195–204 (1989).
Grosse et al., Entrainment of Syrian hamster circadian activity rhythms by neonatal melatonin injections, Am. J. Physiol. 270:R533–R540 (1996).
Haas et al., A simple perfusion chamber for the study of nervous tissue slices in vitro, J. Neurosci. Methods 1:323–325 (1979).
Hastings et al., Non–photic phase shifting of the circadian activity rhythms of Syrian hamsters: the relative potency of arousal and melatonin. Brain Res. 591:20–26 (1992).
Jiang et al., Melatonin activates an outward current and inhibits Ih in rat suprachiasmatic nucleus neurons, Brain Res. 687:125–132 (1995).
Karschin et al., Distribution and localization of a G protein–coupled inwardly rectifying K+ channel in the rat, FEBS Lett. 348:139–144 (1994).
Kelley et al., Coupled reverse transcription–polymerase chain reaction (RT–PRC) technique is comparative, . . . Alcohol 10:185–189 (1993).
Klein, The mammalian melatonin rhythm generating system. In: Light and Biological Rhythms in Man, Wettereberg, L., ed. (New York:Pergamon Press) pp 55–71 (1993).
Laird et al., Simplified mammalian DNA isolation procedure, Nucl. Acids Res. 19:4293 (1991).
Lewy et al., Melatonin shifts human circadian rhythms according to a phase–response curve, Chronobio. Int., 9:380–392 (1992).
Li et al., Targeted mutation of the DNA methyltransferase gene results in embryonic lethality, Cell 69:915–926 (1992).
Liu et al., Cholinergic regulation of the suprachiasmatic nucleus circadian rhythm via a muscarinic mechanism at night, J. Neurosci. 16:744–751 (1996).
Mason et al., The electrophysiological effects of melatonin and a putatuve antagonist (N–acetyltryptamine) on rat suprachiasmatic neurones in vitro, Neurosci. Lett. 95:296–301 (1988).
McArthur et al., Melatonin directly reset suprachiasmatic circadian clock in vitro, Brain Res. 565:158–161 (1991).
McArthur et al., Melatonin action and signal transduction in the rat suprachiasmatic circadian clock: activation of protein kinase C at dusk and dawn, Endocrinology 138:627–634 (1997).

(List continued on next page.)

*Primary Examiner*—Deborah Crouch
*Assistant Examiner*—Joseph T. Woitach
(74) *Attorney, Agent, or Firm*—Fish & Richardson P.C.

(57) ABSTRACT

Disclosed are mice containing a targeted disruption of various melatonin receptor subtypes, and methods of using the mice to identify agonists and antagonists of melatonin.

11 Claims, 12 Drawing Sheets

OTHER PUBLICATIONS

Meister et al., Multineuronal signals from the retina: acquisition and analysis, J. Neurosci. Methods 51:95–106 (1994).

Morgan et al., Both pertussis toxin sensitive and insensitive G proteins link melatonin receptors to inhibition of adenylyl cyclase in the ovine pars tuberalis. J. Neuroendocrinol. 2:773–776 (1990).

Nelson et al., Melatonin recptors activate heteromeric G–protein coupled Kir3 channels, NeuroReport 7:717–720 (1996).

Palm et al., Correction of non–24–hour sleep/wake cycle by melatonin in a blind retarded boy, Ann. Neurol. 29:336–339 (1991).

Petrie et al., Effects of melatonin on jet lag after long haul flights, Br. Med. J. 298:705–707 (1989).

Prosser et al., Serotonergic phase advances of the mammalian circadian clock involve protein kinase A and K+ channel opening, Brain Res. 644:67–73 (1994).

Reppert et al., Molecular characterization of a second melatonin receptor expressed in human retina and brain: The Mel lb–melatonin receptor, Proc. Natl. Acad. Sci. USA 92:8734–8738 (1995).

Roca et al., Structure, characterization, and expression of the gene encoding the mouse Mel I a melatonin receptor, Endocrinology 137:3469–3477 (1996).

Sack et al., Melatonin administration to blind people: Phase advances and entrainment, J. Biol Rhythms 6:249–261 (1991).

Shibata et al., Effects of melatonin on neuronal activity in the rat suprachiasmatic nucleus in vitro, Neurosci. Lett. 97:140–144 (1989).

Siuciak et al., Autoradiographic localization of 2–[1251]–iodomelatonin binding sites in the brains of C3H/HeN and CS7RT J strains of mice, Eur. J. Pharmacol. 180:387–390 (1990).

Starkey et al., Melatonin and 5–hydroxytrptamine phase–advance the rat circadian clock by activation of nitric oxide synthesis. Neurosci. Lett. 211:199–202 (1996).

Starkey et al.,Modulation of the rat suprachiasmatic circadian clock by melatonin in vitro, NeuroReport 6:1947–1951 (1995).

Stehle et al., Effects of melatonin on spontaneous electrical activity of neurons in rat suprachiasmatic nuclei: an in vitro iontophoretic study, J. Neural Transm. 78:173–177 (1989).

Vanecek et al., Melatonin inhibits gonadotropin–releasing hormone–induced elevation of intracellular Ca+2 in neonatal rat pituitary cells, Endocrinology 130:701–707 (1992).

Van Reeth et al., Stimulated activity mediates phase shifts in the hamster circadian clock induced by dark pulses of benzodiazepines. Nature 339:49–51 (1989).

Weaver et al., The $Mel_{1a}$ melatonin receptor gene is expressed in human suprachiasmatic nuclei, NeuroReport 8:109–112 (1996).

Weaver et al., Nature's knockout: The Mel lb receptor is not necessary for reproductive and circadian responses to melatonin in Siberian hamsters, Mol. Endocrinol. 10:1478–1487 (1996).

Wickman et al., Ion channel regulation by G proteins, Physiol. Rev. 75:865–885 (1995).

* cited by examiner

```
                                                                          cggaggatg   -1158
acctgaacctctgatcctttgccttccctcctgggtgctgactgaggtgccacatccagtttatacagcactagaaatg   -1068
gagtctaagatttgcaaatgctgcacgagcctcagcgctccacacgcctcagccccctcaattctgcattgcatttcttga   -978
aattattgataacacaaccattttacttactttgttgagacaggattttgagaccaggatttatacagcacatgttaatga   -888
gccccaaactgtgtgattctctcctgcctccagctccagctacgacatgttcttaattaatacagatttaatatgtcatgc   -798
atgctttctgtattcatcttctcttaaaatgcatgaaaatttaagtgttcaattttcttcactcttcaaaggacttgtaagtcctcccatgttga   -708
cagccataaaatatatggagagacatgaaacatcatatgtttgtgtaagtctcccatgttgaa   -618
gaaagttttgggttttctgttttcactgataglttccaaaagaacatatacaccctgtcatctgcaaatatttactattgccca   -528
atctcaagtttctgttttctcactgatagtttcaaaagaacatatacaccctgtcatctgcaaatatttattcattgcca   -438
gaaacacccagaacagaacattaaatcgctatgccagacggaaaggtgtgattttaatactattactttattcccacattg   -348
actattaaagttgatgagttgagttctatttctcaagcatctagtctcctcacacggggcgcaacgtg   -258
cgtgaatcgagccttccagggtgcaagttcttccctgcaagttcctcaccgcatctagtctcctcacacggggcgcaacgtg   -168
cacgcactgtgggaccctccagtccagtgctggcagtgctggcagtgtcagcaggcggaggcacagagg   -78
                                                                          * exon 1 ->
taccaccgggaggggctgagtgggcaggacagccgcgaagcaatcataaggatgcaaagtagacgcggagggcCATAAAAGTGGCG   +13
                                         AT Rich Region
GAGAGGCTCGAGCAGAGCTGAGCAGTTGAGGGCTCCCGGGGCGCACAGAGACAATGGCCCCTGCGTGCGGGAGGACC   +103
           XhoI
ATGAAGGGCAATGTCAGCGAGCTGCTCAATGCCACTCAGCAGGCTCCAGGCGGCGGGGAGGAGGGAGACCGTCTGCTGCC   +193
 M K G  N V S  E L L  N A T  Q Q A P G G G E E G R R P  S W L A              30
TCTACACTGGCCTTCATCCTCTTACCATCGTGGTGGACATTCTCGGCAACCTGCTCGTGTCATCCTCTGTGTTAGCTCAGTCAAGAAG   +283
 S T L A F I L F T I V V D I L G N L L V I L S V Y R N K K                    60
                                                                                  | exon 2 ->
 <- exon 1 |                                                     CTCAGGAATATATTTGTGTG   +313
CTCAGGAACTCAGgtagggctccggg.........intron >13 kb.........ctctcctcagGAATATATTTGTGTG
 L R N S G                                                     N I F V V     70
AGTTTAGCTGTGGCAGACCTCGTGGTAGCTGTGGCTGTGTTACCCTGTTGTCTGCTGACATCTATCCTTAACAACGGATGGAATCTGGATAT   +403
 S L A V A D L V V A V Y P Y P L V L T S  I L N N G W N L G Y               100
                II                                                      III
CTACACTGTCAAGTCAGCGCATTTCTAAATGGCTTGAGTGTCATCGGCTCGATATTCAACATCACGGGGATCGCTATGAACCGTTACTGC   +493
 L H C Q V  S A F L M G L S V I G S I F N I T G I  A M N R Y C             130

FIG. 1A
```

```
TACATTTGCCACAGCCTCAAGTACGACAAAATATACAGTAACAAGAACTCGCTCTACGTGTTCCTGATATGGATGCTGACACTCATC    +583
 Y  I  C  H  S  L  K  Y  D  K  I  Y  S  N  K  N  S  L  C  Y  V  F  L  I  W  M  L  T  L  I    160
                        IV

GCCATCATGCCCAACCTGCAAACCGGAACACTGCAATACGATCCCGATCCAGTCGTACTTCACCCAGTCTGTCAGCTCAGCGTAC        +673
 A  I  M  P  N  L  Q  T  G  T  L  Q  Y  D  P  R  I  Y  S  C  T  F  T  Q  S  V  S  S  A  Y    190

ACGGATAGCAGTGGGTGGTTTTCCATTTCATCTGTCCTATGATTATTGTCATCTTCTGTACTTAAGGATATGGTCTCGTCCTTCAGGTC   +763
 T  I  A  V  V  V  F  H  F  I  V  P  M  I  I  V  I  F  C  Y  L  R  I  W  V  L  V  L  Q  V    220
                        V

AGACGGAGGGTGAAACCCGACAACAAGCCCAAACTGAAGCCCCAGGACTTCAGGAACTTCGTCACCATGTTCGTAGTTTTTGTACTTTTT  +853
 R  R  R  V  K  P  D  N  K  P  K  L  K  P  Q  D  F  R  N  F  V  T  M  F  V  V  F  V  L  F    250

GCCATTTGTTGGGCCCCACTCAACCTCATAGTCTTATTGTGGCTCCCCAGATCCCCAGAGTGGCTGTTC                        +943
 A  I  C  W  A  P  L  N  L  I  G  L  I  V  A  S  D  P  A  T  M  V  P  R  I  P  E  W  L  F    280
            VI

GTGGCTAGTTACTACCTGGCGTACTTCAACAGCTGCCTTCAACAGCGCAATTATATACGGACTGCTGAATCAGAATTTCAGAAAGGAATACAAA +1033
 V  A  S  Y  Y  L  A  Y  F  N  S  C  L  N  A  I  I  Y  G  L  L  N  Q  N  F  R  K  E  Y  K       310
            VII

AAGATTATTGTCTCGTTGTGCACAGCCAAGATGTTCTTTGTGGAGAGTTCAATGAAGAAGCAGATAAGATTAAATGTAAGCCCTCTCCA      +1123
 K  I  I  V  S  L  C  T  A  K  M  F  F  V  E  S  S  N  E  E  A  D  K  I  K  C  K  P  S  P       340

CTAATACCCAATAATAACTTAATAAAGGTGACTCTGTTTAAAAAGCCAGTGTGCTAGCAGATTATCCACACTGGTTGGGGTCTCCTG        +1213
 L  I  P  N  N  N  L  I  K  V  D  S  V     - (SEQ ID NO:2)                                      353

CTCTCCTTGTTGTTGCTTCTTCTTTTGTCTAGAAATCAGTTCTATCCAACTTGAAGCTCTTCAGGGTTGCCTCCATAGTGTTGAAAGGATTCC   +1303
TGTCTGCCCCATAATCAGATATTGCTAGTATCAAGGGGAATGCTGAACAGGCACACCTAGTTTAAATGACAACTTGTATCAGCAGGAG        +1393
GTCGTGGTGTCAGACTCTCTGTCTGTCTTGGGCAACCAGTCTTGCCACACATTTAGGATTACAATATACAACACAGACCAAACC            +1483
TGAACAAATGTGAAGAACTGGAAGAGGAGACCATGGGGACCTTCCTTTTATTGTAAGCGAGTGATACAGAGTGTTTATTCTTAC            +1573

CTATGGCTGAATTAAAATAGTCAAAAAACTTAA (SEQ ID NO:1)                                                 +1606
       Poly(A) signal
           <-- exon 2
```

FIG. 1B

```
      ATGCCTGAGAACAGCTCAATCCCTAACTGCTGTGAGGCCAGCGGGCTGGCAGCGCGCCT
   1  ------------+---------+---------+---------+---------+---------+  60 a     M  P  E  N  S  S  I  P  N  C  C  E  A  S  G  L  A  A  R  P   -

AGTTGGTCTGGGTCAGCCGGAGCCAGGCCCCCTGTGACTGCCCGGGCCCCCTGGGTGGCT
  61  ------------+---------+---------+---------+---------+---------+ 120 a     S  W  S  G  S  A  G  A  R  P  P  V  T  A  R  A  P  W  V  A   -

CCCATGCTATCTACAGTAGTCGTCGTCACCACAGCCGTGGACTTCGTGGGGAACCTGCTT
 121  ------------+---------+---------+---------+---------+---------+ 180 a     P  M  L  S  T  V  V  V  T  T  A  V  D  F  V  G  N  L  L   -

GTCATCCTCTCAGTGCTCAGGAACCGCAAGCTGCGGAACGCAGGTAATTTGTTTGTGGTG
 181  ------------+---------+---------+---------+---------+---------+ 240 a     V  I  L  S  V  L  R  N  R  K  L  R  N  A  G  N  L  F  V  V   -

AGTCTGGCCTTGGCTGACTTGGTGATAGCCTTGTACCCTTACCCACTGATCCTTGTGGCC
 241  ------------+---------+---------+---------+---------+---------+ 300 a     S  L  A  L  A  D  L  V  I  A  L  Y  P  Y  P  L  I  L  V  A   -

ATTATCCGTGACGGTTGGGTCCTTGGGGAGGCCCACTGCAAGGCCAGTGCCTTTGTGATG
 301  ------------+---------+---------+---------+---------+---------+ 360 a     I  I  R  D  G  W  V  L  G  E  A  H  C  K  A  S  A  F  V  M   -

GGCCTGAGTGTCATTGGCTCTGTCTTCAACATCACAGCCATTGCCATCAACCGCTACTGC
 361  ------------+---------+---------+---------+---------+---------+ 420 a     G  L  S  V  I  G  S  V  F  N  I  T  A  I  A  I  N  R  Y  C   -

TGCATCTGTCATAGTACCACCTACCACCGGGTCTGCAGTCACTGGTATACTCCCATCTAC
 421  ------------+---------+---------+---------+---------+---------+ 480 a     C  I  C  H  S  T  T  Y  H  R  V  C  S  H  W  Y  T  P  I  Y   -

ATCAGCCTCGTCTGGCTCCTCACTCTGGTGGCTTTGGTGCCCAATTTCTTTGTGGGGTCT
 481  ------------+---------+---------+---------+---------+---------+ 540
```

FIG. 9A

```
a    I  S  L  V  W  L  L  T  L  V  A  L  V  P  N  F  F  V  G  S    -
     TTAGAGTATGATCCACGCATCTATTCCTGCACCTTCATCCAGACAGCCAGCACACAGTAC
541  ------------+---------+---------+---------+---------+---------+ 600 a    L  E  Y  D  P  R  I  Y  S  C  T  F  I  Q  T  A  S  T  Q  Y    -
     ACGGCAGCTGTGGTGGCCATCCACTTCCTCCTTCCCATGGCTGTGGTGTCCTTCTGCTAC
601  ------------+---------+---------+---------+---------+---------+ 660 a    T  A  A  V  V  A  I  H  F  L  L  P  M  A  V  V  S  F  C  Y    -
     CTGCGAATCTGGGTACTGGTGCTCCAGGCCCGAAGGAAGGCCAAGGCTACGAGGAAGCTG
661  ------------+---------+---------+---------+---------+---------+ 720 a    L  R  I  W  V  L  V  L  Q  A  R  R  K  A  K  A  T  R  K  L    -
     CGTCTGAGACCGAGTGATTTGCGCAGTTTCCTAACCATGTTTGCAGTGTTTGTGGTTTTT
721  ------------+---------+---------+---------+---------+---------+ 780 a    R  L  R  P  S  D  L  R  S  F  L  T  M  F  A  V  F  V  V  F    -
     GCCATATGCTGGGCCCCCCTCAACTGTATCGGCCTTGCAGTGGCCATCAACCCAGAGGCA
781  ------------+---------+---------+---------+---------+---------+ 840 a    A  I  C  W  A  P  L  N  C  I  G  L  A  V  I  N  P  E  A       -
     ATGGCTCTCCAGGTCCCAGAAGGGCTCTTTGTCACCAGTTACTTCTTAGCTTACTTTAAC
841  ------------+---------+---------+---------+---------+---------+ 900 a    M  A  L  Q  V  P  E  G  L  F  V  T  S  Y  F  L  A  Y  F  N    -
     AGCTGCCTTAATGCCATTGTTTATGGCTCCTGAACCAGAACTTCCGCAGGGAGTACAAG
901  ------------+---------+---------+---------+---------+---------+ 960 a    S  C  L  N  A  I  V  Y  G  L  L  N  Q  N  F  R  R  E  Y  K    -
     AGGATCCTTTTGGCCATATGGAACACTAGGCGCTGCATACAGCATGCTTCCAAACACTGT
961  ------------+---------+---------+---------+---------+---------+ 1020 a    R  I  L  L  A  I  W  N  T  R  R  C  I  Q  H  A  S  K  H  C    -
     CTTACTGAGGAGCGACAGGGCCCGACGCCACCTGCTGCCAGGGCTACCGTGCCTGTCAAG
1021 ------------+---------+---------+---------+---------+---------+ 1080 a    L  T  E  E  R  Q  G  P  T  P  P  A  A  R  A  T  V  P  V  K    -
     GAAGGTGCTCTCTAG    (SEQ ID NO:12)
1081 ----------+---- 1095

FIG. 9B a    E  G  A  L  *   -  (SEQ ID NO:13)
```

MELATONIN RECEPTOR-DEFICIENT MICE AND USES THEREOF

This application is a divisional of application Ser. No. 09/122,527, filed Jul. 24, 1998 now abandoned, which claims priority from provisional application 60/053,565 filed Jul. 24, 1997.

STATEMENT AS TO FEDERALLY SPONSORED RESEARCH

This invention was made with government support under grants R37 HD14427 and DK42125, awarded by the National Institutes of Health. The Government has certain rights in the invention.

BACKGROUND OF THE INVENTION

The field of the invention is melatonin and its receptors.

Melatonin, the principal hormone of the pineal gland, influences the timing of mammalian circadian rhythms and regulates the reproductive alterations that occur in response to changes in day length in seasonally breeding mammals (Reppert, S. M. and Weaver, D. T., *Cell* 83:1059–1062, 1995). In humans, melatonin administration has been shown to alleviate the symptoms of jet lag after air travel across several time zones. The hormone also has potent sedative effects in humans and may be a useful hypnotic agent.

Melatonin exerts these effects through specific guanine nucleotide binding protein,(G protein)-coupled receptors. A family of these G protein-coupled melatonin receptors has been cloned from *Xenopus laevis*, chicken and various mammals (U.S. applications Ser. Nos. 08/261,857, filed Jun. 17, 1994; 08/319,887, filed Oct. 7, 1994; and 08/466,103, filed Jun. 6, 1995; Ebisawa, T., et al. *Proc. Natl. Acad. Sci. USA* 91:6133–6137, 1994; Reppert, S. M. et al., *Neuron* 13:1177–1185, 1994; Reppert, S. M. et al. *Proc. Natl. Acad. Sci. USA* 92:8734–8738, 1995; Reppert, S. M. et al., *Neuron* 15:1003–1015, 1995). These cloned receptors exhibit affinity and pharmacological characteristics similar to each other and to endogenous receptors, as defined by the melatonin agonist 2- $[^{125}I]$-iodomelatonin ($^{125}$,-Mel). Two mammalian melatonin receptor subtypes have been identified by molecular cloning studies. The mammalian receptor $Mel_{1a}$ is expressed in the hypothalamic suprachiasmatic nuclei (SCN) and hypophyseal pars tuberalis, which are presumed sites of the circadian and some of the reproductive actions of melatonin, respectively (Reppert, S. M. et al., *Neuron* 13:1177–1185, 1994). The mammalian $Mel_{1b}$ receptor is expressed in retina and brain and may mediate the reported effects of melatonin on retinal physiology in mammals (Reppert, S. M. et al. *Proc. Natl. Acad. Sci. USA* 92:8734–8738, 1995). A third receptor subtype, the $Mel_{1c}$ melatonin receptor, has been cloned from zebrafish, Xenopus, and chicken, but not from mammals (Reppert, S. M. et al., *Neuron* 15:1003–1015, 1995).

SUMMARY OF THE INVENTION

Mice that are engineered to lack various melatonin receptor subtypes have been generated in accordance with the present invention. Since melatonin can entrain circadian rhythms, the mice of the invention are useful for elucidating the roles of the different receptors in entrainment and control of biological rhythms, including jet lag, disturbed sleep-wake cycle in blind people, sleep disorders in shift workers, establishing a diurnal sleep-wake pattern in neonates, and regulating the initiation and timing of puberty in humans and the mating cycles of seasonally breeding mammals.

In general, the invention features a transgenic non-human animal having a transgene disrupting expression of a melatonin receptor gene, the transgene being chromosomally integrated into the germ cells of the animal, e.g., where the mammal is a mouse and where the melatonin receptor gene encodes the melatonin 1a receptor, or the melatonin 1b receptor. The cells can be homozygous for the transgene, and the disruption can result in a null mutation. The cells can be used to produce a cell line.

In another aspect, the invention features a method of determining if a candidate compound exerts an effect via a melatonin receptor other than the melatonin 1a receptor, the method comprising contacting suprachiasmatic nuclei of the mouse containing the disrupted melatonin 1a receptor gene with the candidate compound, and measuring the phase shift in the suprachiasmatic nuclei, wherein an effect on phase shift in the presence of the candidate compound is an indication that the candidate compound exerts an effect via a melatonin receptor other than the melatonin 1a receptor.

In yet another aspect, the invention features a method of determining if a candidate compound is a melatonin 1b receptor antagonist, the method comprising contacting suprachiasmatic nuclei of the mouse containing the disrupted melatonin 1a receptor gene with melatonin in the presence of the candidate compound, and measuring the phase shift in the suprachiasmatic nuclei, wherein a decrease in phase shift in the presence of both melatonin and the candidate compound, relative to that seen in the presence of melatonin but the absence of the candidate compound, is an indication that the candidate compound is a melatonin antagonist.

The invention also features a method of determining if a candidate compound exerts an effect via the melatonin 1a receptor, the method comprising contacting suprachiasmatic nuclei of the mouse containing the disrupted melatonin 1b receptor gene with the candidate compound, and measuring the suprachiasmatic nuclei neuronal firing, wherein a decrease in suprachiasmatic nuclei neuronal firing in the presence of the candidate compound, relative to that seen in the absence of the candidate compound, is an indication that the candidate compound exerts an effect via the melatonin 1a receptor.

In yet another aspect, the invention features a method of determining if a candidate compound is a melatonin 1a receptor antagonist, the method comprising contacting suprachiasmatic nuclei of the mouse containing the disrupted melatonin 1b receptor gene with melatonin in the presence of the candidate compound, and measuring the suprachiasmatic nuclei neuronal firing, wherein an increase of the suprachiasmatic nuclei neuronal firing in the presence of the candidate compound, relative to that seen in melatonin-treated cells in the absence of the compound, is an indication that the candidate compound is a melatonin 1a receptor antagonist.

Melatonin's inhibition of neuronal firing is likely due to activation of potassium channels (Wickman, K., and Clapham, D. E., *Physiol. Rev.* 75:865–885, 1995; Jiang, Z.-G., et al., *Brain Res.* 687:125–132, 1995), therefore, the invention also features a method of treating a patient having a condition characterized by suprachiasmatic neuronal firing, the method comprising administering to the patient an effective amount of a potassium channel activator. The condition to be treated can be benign prostatic hyperplasia, jet lag, or disturbed sleep-wake cycle, such as that found in blind people, shift workers, or neonates.

In another aspect, the invention features a method of treating a patient having a condition characterized by suprachiasmatic neuronal firing, without affecting the patient's circadian rhythm, the method comprising administering to the patient an effective amount of a potassium channel activator.

The invention also features a method of controlling the estrus cycle of a mammal, the method comprising administering to the mammal an amount of a potassium channel activator effective to induce or maintain the mammal's estrus cycle.

By "high-affinity melatonin receptor polypeptide" is meant all or a functional part of a vertebrate cell surface protein which specifically binds melatonin and signals the appropriate melatonin-mediated cascade of biological events (e.g., a decrease in intracellular cAMP concentration). The polypeptide is characterized as having the ligand binding properties (including the agonist and antagonist binding properties) and tissue distribution described herein.

By "homologous recombination" is meant site-specific insertion or deletion of nucleic acid by a mechanism involving matching up of complementary regions in two different DNA molecules.

By "mutation" is meant a change in a nucleic acid sequence or amino acid sequence, e.g., a deletion, an insertion, a translocation involving one or more exons, introns, or transcription regulatory regions (e.g., a promotor) of a gene. If the mutation reduces the expression or activity level of the protein encoded by the mutated gene (all isoforms included) by more than 80% relative to the unmutated gene, the mutation is called a null mutation, and the mouse harboring the mutation is a knockout mouse.

By "target gene" is meant a gene in a cell, which gene is to be modified by homologous recombination with a targeting vector.

By "targeted gene" is meant a gene in a cell, which gene has been modified by homologous recombination with a targeting vector.

By "targeting vector" is meant a DNA molecule that includes the nucleotide sequence to be incorporated into the target gene, and one or more selectable markers.

By "wild-type control animal" is meant a non-gene-targeted, non-human mammal of the same species as, and otherwise comparable to (e.g., similar age), a gene-targeted non-human mammal. A wild-type control animal is used as the basis for comparison, in assessing results associated with a particular genotype.

BRIEF DESCRIPTION OF THE DRAWINGS

FIG. 1 is a diagram of the nucleotide sequence of the mouse $Mel_{1a}$ receptor cDNA. Nucleotide sequence is numbered from the major transcription start site which defines the start of the first exon. In the coding region, consensus sites for N-linked glycosylation (oval) are indicated and the transmembrane regions are underlined. In the 3' untranslated region, an ATTTA sequence (bold print) and consensus sequence for polyadenylation signal (underlined) are highlighted. The nucleotide (SEQ ID NO:1) and amino acid (SEQ ID NO:2) numbers are to the right of each line. The sequence has been deposited in GenBank under accession number U52222.

FIG. 5A and 5B illustrate single-unit electrical activity rhythms in SCN slices from wild-type (+/+, 5A) and homozygous mutant (−/−, 5B) mice exposed to vehicle from circadian time 9.5–10.5 (open vertical bars). 5C illustrates the firing rate rhythm of an SCN slice from a homozygous mutant mouse exposed to melatonin (1 nM) from circadian time 9.5–10.5 (hatched vertical bar), which resulted in an approximately 4-hour phase advance in the firing rate rhythm. The dotted vertical line in the far right panel of each figure represents the average time of peak electrical activity, used as a reference point to show the phase shift between the control (5A and 5B) and experimental mice (5C). Data are representative of 3 studies per treatment. Arrows indicate time of slice preparation. The dark period of the light-dark cycle in the animal room is indicated by the hatched horizontal bars at the top of each panel.

FIG. 9 is a diagram of the nucleotide sequence (SEQ ID NO:12) and amino acid sequence (SEQ ID NO:13) of the mouse $Mel_{1b}$ receptor CDNA. The sequence is numbered starting from the major transcription start site.

DETAILED DESCRIPTION

Non-human mammals which are engineered to lack various melatonin receptor subtypes are useful for elucidating the roles played by the various receptor subtypes in controlling circadian rhythms, including inhibition of suprachiasmatic nuclei neuronal firing, and phase-shifting and entraining of biological rhythms. Such animals are therefore useful to develop therapeutics to treat conditions such as jet lag, facilitate reentrainment of some endogenous melatonin rhythms, synchronize the disturbed sleep-wake cycle of blind people, alleviate sleep disorders in shift workers, facilitate the emergence of a diurnal sleep-wake pattern in neonates, regulate ovarian cyclicity in human females, control the initiation and timing of puberty in humans, and control the onset of the mating cycle in seasonally breeding animals, such as sheep.

EXAMPLES

The following description of the making of melatonin receptor-deficient mice, and methods for their use, are provided for the purpose of illustrating the invention, and should not be construed as limiting.

Example 1

Targeted disruption of the $Mel_{1a}$ receptor

The mouse $Mel_{1a}$ receptor gene is composed of two exons divided by a large (>13 kb) intron (Roca, A. L., et al., *Endocrinology* 137:3469–3477, 1996). A 15 Kb genomic clone encoding part of the Melia receptor was isolated from a mouse 129/Sv genomic library (Stratagene) using a probe generated from exon 1 of the $Mel_{1a}$ receptor gene (SEQ ID NO:1), which is shown in FIG. 1. FIG. 1 illustrates the mouse $Mel_{1a}$ receptor gene, including the complete nucleotide and amino acid sequences (SEQ ID NO: 1 AND SEQ ID NO:2, respectively). The genomic clone, as diagrammed in FIG. 2, contains about 11.5 kb of DNA 5' of exon 1, exon 1 (0.6 kb, containing the translation start codon and encoding amino acids up to the first intracellular loop), and about 3.5 kb of the large intron that separates the two exons. This genomic clone was subcloned into the NotI site of pBluescript (Stratagene). The first exon was subsequently removed by restriction digestion with StuI and Eco47III. SalI adapters were ligated to the blunt ends to allow PGK-Neo (digested with XhoI-SalI) to be inserted in place of receptor exon 1. The 15 kb insert of the targeting vector, containing PGKNeo, was then excised from the plasmid with NotI and used for electroporation of J1 ES cells as previously described (Li, E., et al., *Cell* 69:915–926, 1992). Of 220 G418-resistant ES clones isolated, 27 contain the targeted allele based on Southern blots of genomic DNA digested with either EcoRV or SpeI and probed with a 3' flanking probe not contained within the genomic clone.

Figure 2:
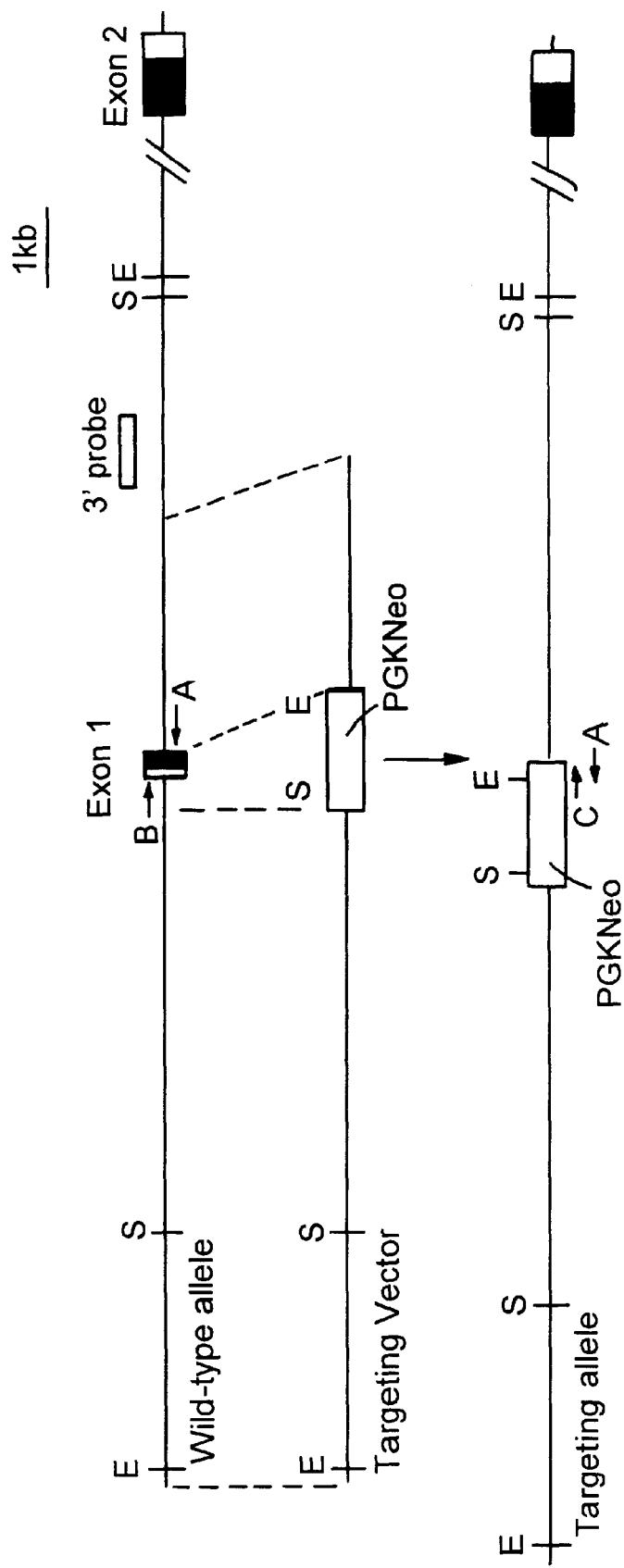
FIG. 2 is a diagram illustrating the targeted disruption of the mouse Mella melatonin receptor gene. The receptor gene with exons (in boxes) and relevant restriction sites is depicted. The position of the 3' probe used for Southern analysis is indicated. The center diagram illustrates the targeting construct in which Exon 1 has been replaced by a cassette (PGKNeo) containing a promoter-driven neomycin-resistance gene. The bottom schematic represents the targeted allele integrated into the genome by homologous recombination. E=EcoRV; S=SpeI.

Two targeted ES clones were injected into C57BL/6J blastocysts (Bradley, A., in: *Teratocarcinomas and Embryonic Stem Cells*, Robertson, E. J., ed., IRL Press, Oxford, England, pp. 113–151, 1987) to generate chimeras. Chimeric males were bred to C57BL/6J females, and germline transmission of the mutant allele was detected by Southern blot analysis or PCR of tail DNA (prepared as described by Laird, P. W., et al., *Nucl. Acids Res.* 19:4293, 1991) from $F_1$ offspring with agouti coat color. The amplification primers consisted of a cocktail of the A, B, and C primers as shown in FIG. 2. The wild-type allele (primers A–B) produces a 480 bp product, while the disrupted allele (Primers A–C) produces a 240 bp product. Germline transmission was obtained from both clones.

Genotyping by Southern Blot Analysis Genomic DNA was digested with either EcoRV or SpeI and separated by electrophoresis through a 0.8% agarose gel. DNA was alkaline denatured and transferred to GeneScreen plus membrane (Dupont/NEN) by capillary action. Membranes were hybridized with a PCR-generated 1.0 kb DNA fragment 3' of the targeted DNA (as shown in FIG. 2), labeled with [alpha-$^{32}$P]dCTP (2000 Ci/mmol) by random priming. Blots were washed with 0.2×SSC and 0.1% SDS at 65° C.

Genotyoing by PCR Analysis

Genomic DNA was subjected to 35 cycles of amplification using incubations at 94° C. for 45 sec, 60° C. for 45 sec and 72° C. for 3 minutes. The amplified DNA was separated on an agarose gel. The primers used for genotyping were:

A, 5'-GAG TCC AAG TTG CTG GGC AGT GGA-3' (SEQ ID NO:3);

B, 5'-GAA GTT TTC TCA GTG TCC CGC AAT GG-3' (SEQ ID NO:4); and

C, 5'-CCA GCT CAT TCC TCC ACT CAT GAT CTA-3' (SEQ ID NO:5). Location of the primers is shown in FIG. 2. $^{125}$I-Mel in vitro Autoradiography Male mice were housed in ventilated environmental compartments with a light:dark (LD) schedule of 12:12. Animals were killed by decapitation in the afternoon, 3 to 5 hours before lights-off, at 4–7 weeks of age. Brains were removed, frozen in cooled (−20° C.) 2-methylbutane, and stored at −80° C. until sectioning in a Bright-Hacker cryostat.

Fifteen-micron coronal sections were collected as a 1-in-8 series throughout the entire brain from 3 wild-type (+/+), 2 heterozygous mutant (+/−), and 2 homozygous mutant (−/−) mice. Sections encompassing the hypothalamus were collected from an additional 1 wild-type, 8 heterozygous mutant, and 3 homozygous mutant mice. All tissue sections were processed for the melatonin agonist 2-[$^{125}$I]-iodomelatonin ($^{125}$I-Mel) binding in a single run. One series (sections at 120 μm intervals) from each animal was processed for total $^{125}$I-Mel binding (100 pM $^{125}$I-Mel), and an adjacent series of sections was processed for nonspecific binding (100 pM $^{125}$I-Mel in the presence of 1 μM melatonin) The ligand concentration of 100 pM was used to improve the chances of detection of binding to the $Mel_{1b}$ receptor, which may have lower affinity (KD=160 pM for the human clone). The autoradiographic procedure was as previously described (Reppert, S. M., et al., Neuron 13:1177–1185, 1994). Briefly, sections were preincubated in autoradiography buffer (50 mM Tris-HCl-4mM $MgCl_2$, containing 0.1% BSA) for 1 hour at room temperature, incubated in buffer with 100 pM $^{125}$I-Mel (±1 μM melatonin), then washed (two times, 15 minutes each wash) in ice-cold autoradiography buffer minus BSA, dipped in ice-cold distilled water, and blown dry with a stream of cool air. Sections were exposed to Kodak BioMax MR™ film for 19 days.

Quantitative analysis of autoradiograms was performed using a computer-based image analysis system and the NIH Image program. Radioactivity levels were determined by comparison to $^{125}$1-microscale standards (Amersham) exposed along with the sections on each film.

SCN Multiunit Recordings

Adult male wild-type and homozygous mutant mice were housed in LD 12:12 for a minimum of three weeks prior to experimentation. After the adaptation period, the mice were killed 2.0 to 4.5 hours after lights-on, and brains were rapidly dissected and placed into ACSF medium containing 116.3 mM NaCl, 5,4 mM KCl, 1.0 mM $NaH_2PO_4$, 26.2 mM $NaHCO_3$, 1.8 mM $CaCl_2$, 0.8 mM $MgSO_4$, 24.6 mM dextrose, and 5 mg/l Gentamicin sulphate, pH 7.5. A block of tissue containing the hypothalamus was dissected from the brain and transferred to a manual tissue chopper where coronal hypothalamic brain slices (400 μm in thickness) containing the SCN were prepared. Slices were placed in a Haas-type brain slice chamber (Haas H. L., et al., J. Neurosci. Methods 1:323–325, 1979; Medical Systems Corp.) and gauze strips placed over the slices in the vicinity of the SCN to raise the fluid level above the slices. They were continually superfused with ACSF medium warmed to 37° C. To record multiple-unit SCN electrical activity, a 76 μm-diameter, teflon-coated platinum-iridium wire electrode was lowered into the brain slice in the SCN (Bouskila, Y., and Dudek, F. E., Proc. Natl. Acad. Sci. USA 90:3207–3210, 1993). This electrical activity was amplified, and the number of electrical events was counted with a window discriminator (Fintronics Inc., Orange, Conn.). Data were collected and analyzed by computer, using Brainwave™ (Data Waver Technologies, Broomfield, Colo.) or Spike 2™ (Cambridge Electronic Design, Cambridge, Mass.) software. The average number of electrical events in successive 1-minute intervals was determined and plotted against the circadian time of recording. Slices were excluded if their viability was compromised on day 2 of recording.

Melatonin was prepared as a 100 μM stock solution in 100% ethanol, which was serially diluted with ACSF medium to yield four melatonin concentrations between 0.1 and 100 nM. A stock solution of vehicle (100% ethanol) was serially diluted with ACSF medium to yield the corresponding vehicle for each melatonin concentration. Melatonin or vehicle was applied by gravity flow in the bath for 30 minutes at each concentration before switching to the next solution. In preliminary experiments, it was found that 30 minutes of melatonin application was sufficient to produce maximal inhibition of firing in SCN slices from rats. In the mouse experiments at circadian time 4.5–6.5 where only the single highest vehicle concentration was used as a comparator, the vehicle was applied for 30 minutes prior to the application of melatonin. A programmable automatic solution switching system (AutoMate Scientific Inc., Oakland, Calif.) was employed to time solution applications. There were no significant effects of vehicle observed in any of the experiments.

The maximum percent inhibition of SCN neuronal firing during each 30 minutes application of melatonin or vehicle was calculated with respect to the average multiunit firing rate during the 5 minute period prior to the first application of a series, and plotted.

SCN Single Unit Recordings

Mice were housed in LD 12:12 for three weeks prior to experimentation. After adaptation, mice were killed by decapitation during the light phase of the LD cycle. Hypothalamic slices (500 μm) were prepared using a tissue chopper and incubated at 37° C., as previously described (Liu, C., and Gillette, M. U., J. Neurosci. 16:744–751, 1996). For most experiments, perfusion was discontinued during the 1-hour treatment with melatonin or vehicle (0.0001% ethanol in perfusion medium). For the pertussis toxin experiment, perfusion was discontinued for 6 hours, ending after the vehicle or melatonin treatment. At the end of treatment, the medium in the chamber was replaced, and perfusion was resumed with melatonin-free medium. Single units from the SCN were recorded the following day with glass microelectrodes (Liu, C., and Gillette, M. U., J. Neurosci. 16:744–751, 1996). Signals were amplified, filtered to a band width of 0.3–3 kHz, and stored (MacADIO II, GW Instruments, Somerville, Mass.). Voltage pulses exceeding preset recording threshold were detected on-line by custom software. Off-line analysis assigned a cluster of spikes of similar amplitude and width to each unit recorded (Meister, M., et al., J. Neurosci. Methods 51:95–101, 1994). Firing rate data were analyzed as previously described to determine the time-of-peak in the activity rhythm (Liu, C., and Gillette, M. U., J. Neurosci. 16:744–751, 1996).

Drugs $^{125}$I-Mel and other radioisotopes were purchased from New England Nuclear (Boston, Mass.). Non-radioactive 2-Iodomelatonin was purchased from Research Biochemicals, Inc. (Natick, Mass.). All other drugs were purchased from Sigma (St. Louis, Mo.).

Results

The $Mel_{1a}$ receptor gene mutation appears to have no effect on survival. Of the first 501 pups born from breeding heterzygotes, 131 (26.2%) were homozygous for the receptor mutation. Within each of the two ES cell lines generated, the ratio of genotypes from breeding heterozygotes did not differ from the expected Mendelian ratio of 1:2:1 (p>0.05, Chi-square test). Both male and female homozygous mutants are fertile.

Because the $Mel_{1a}$ receptor is normally expressed in the SCN (Reppert, S. M., et al., *Neuron* 13:1177–1185, 1994) and thus potentially is involved in biological responses of the circadian clock, circadian function was assessed in homozygous mutants. No significant abnormalities in circadian function were detected in homozygous mutant mice. The mutant mice exhibited robust circadian rhythms (of appropriate phase and amplitude) in wheel-running behavior that entrained to the light-dark cycle. Assessment of the period (cycle) length of the activity rhythm in constant darkness showed no significant difference between homozygous mutant mice (period length=23.47±0.10 hrs; mean±SEM, n =12) and wild-types (23.49±0.08 hrs; n=15).

Neither 129/Sv or C57BL/6 mice make melatonin. Like many strains of laboratory mice, these strains appear to have a genetic defect in pineal melatonin biosynthesis (Goto, M., et al., *J. Pineal Res.* 7:195–204, 1989). Nonetheless, wild-type mice of 129/Sv/C57BL/6 hybrid genetic background have a normal complement of high-affinity melatonin receptors as assessed by $^{125}$I-Mel in vitro autoradiography. In addition, as described below, the SCN of these mice exhibit robust responses to melatonin in the two in vitro assay systems that we employ in our studies.

To determine whether the $Mel_{1a}$ receptor gene is inactivated in homozygous mutants, $^{125}$I-Mel in vitro autoradiography was used. This method is the most sensitive means currently available to evaluate the presence of high-affinity melatonin receptors in individual brain nuclei (Weaver, D. R., et al., In: Klein, D. C., et al., eds. *Suprachiasmatic Nucleus: the Mind's Clock*. Oxford Press, New York, pp. 289–308, 1991). Because $Mel_{1a}$ receptor MRNA is found in brain areas in which $^{125}$I-Mel binding is detected, targeted disruption of the $Mel_{1a}$ receptor should eliminate $^{125}$I-Mel branding in mouse brain.

Binding of $^{125}$I-Mel was first evaluated in wild-type mice. These mice exhibited a very restricted pattern of $^{125}$I-Mel binding in brain, similar to that described in other rodents (Weaver, D. R., et al., In: Klein, D. C., et al., eds. *Suprachiasmatic Nucleus: the Mind's Clock*. Oxford Press, New York, pp. 289–308, 1991). The most intense specific binding was observed in the hypophyseal pars tuberalis (PT) of the pituitary. The SCN, paraventricular nucleus of the thalamus (PVT), and parabigeminal nucleus also contained a high level of specific $^{125}$I-Mel binding. A amoderate level of specific binding was present in the anterior hypothalamus (anterior and lateral to the SCN), in several thalamic nuclei (reuniens nucleus, the nucleus of the stria medullaris, portions of the paratenial and anterodorsal nuclei), and in the caudal half of the nucleus of the optic tract. Lower levels of specific $^{125}$I-Mel binding were detected in the medial portion of the accumbens nucleus, in the central nucleus of the amygdala, and at the lateral border of the anterior pretectal nucleus. Low levels of specific $^{125}$I-Mel binding were detected in several (but not all) wildtype mice in the medial portion of the nucleus of the solitary tract bordering the area postrema and in the midbrain central grey. The distribution of $^{125}$I-Mel binding in wild-type mice is comparable to that previously reported for C57BL/6J mice and is also similar to that reported in strains of mice that make melatonin (C3H/HeN; Siuciak, J. A., et al., *Eur. J. Pharmacol.* 180:387–390, 1990).

In marked contrast to the detection of specific $^{125}$I-Mel binding in several brain regions in wild-type mice, specific $^{125}$I-Mel binding was not detected in any of these sites in homozygous mutant mice. Importantly, by light microscopy, the SCN appeared normal in location and size in homozygous mutants. Visual inspection of the autoradiographs suggested that heterozygous mutant mice have an intermediate level of $^{125}$I-Mel binding. This was confirmed by quantitative in vitro autoradiographic analysis of $^{125}$I-Mel binding in the SCN. The level of specific $^{125}$I-Mel binding in the SCN of heterozygous mice (n=9) was 52.5% that of wild-type mice (n=5; p=0.001, Student's t-test). The reduction of approximately 50% in binding in heterozygous animals suggests an effect of gene dosage on the level of $^{125}$I-Mel binding observed. Preliminary studies of fetal mouse brain and pituitary also revealed that $^{125}$I-Mel binding detected in these structures in wild-type mice was absent in homozygous $Mel_{1a}$ receptor-mutant mice and reduced in heterozygotes. Taken together, the autoradiographic results clearly show that the engineered $Mel_{1a}$ receptor gene mutation is a null allele and that $Mel_{1a}$ receptors normally account for most, if not all, high-affinity melatonin binding in mouse brain.

Figure 3A:
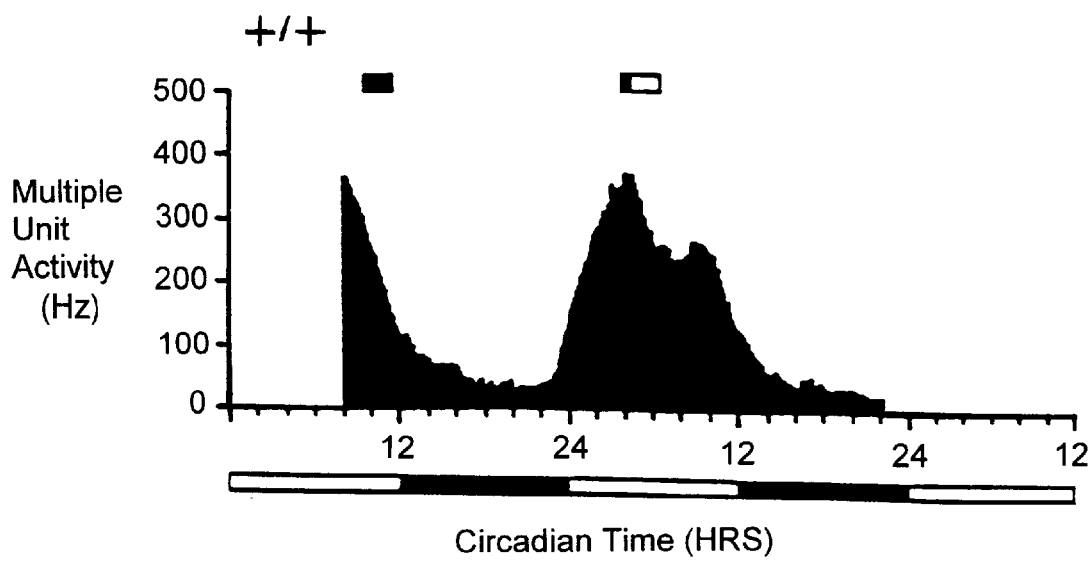
FIGS. 3A and 3B are graphs illustrating melatonin-induced inhibition of multiunit SCN activity in mice. Rhythms of multiunit activity in SCN slices were monitored for 36 hours from wild-type (+/+; 3A) and homozygous mutant (−/−; 3B) mice. The leftmost of the two short horizontal bars above each figure shows the time of treatment (circadian time 9.5–11.5) with vehicle on day 1 in culture. The right-hand horizontal bar above each figure shows the time of vehicle treatment (black portion of bar; circadian time 4.0–4.5) and melatonin treatment (open portion of bar; circadian time 4.5–6.5) on day 2 in culture. Melatonin treatments consisted of consecutive exposures (of 30 minutes each) to 0.1, 1, 10, and 100 nM melatonin. Melatonin induced a suppression of multiunit activity from circadian time 4.5–6.5 in the wild-type slice (3A), while no suppression occurred in the homozygous mutant slice (3B). The horizontal bars below 3B depict the light-dark cycle to which the animals were exposed before sacrifice.
Figure 3B:
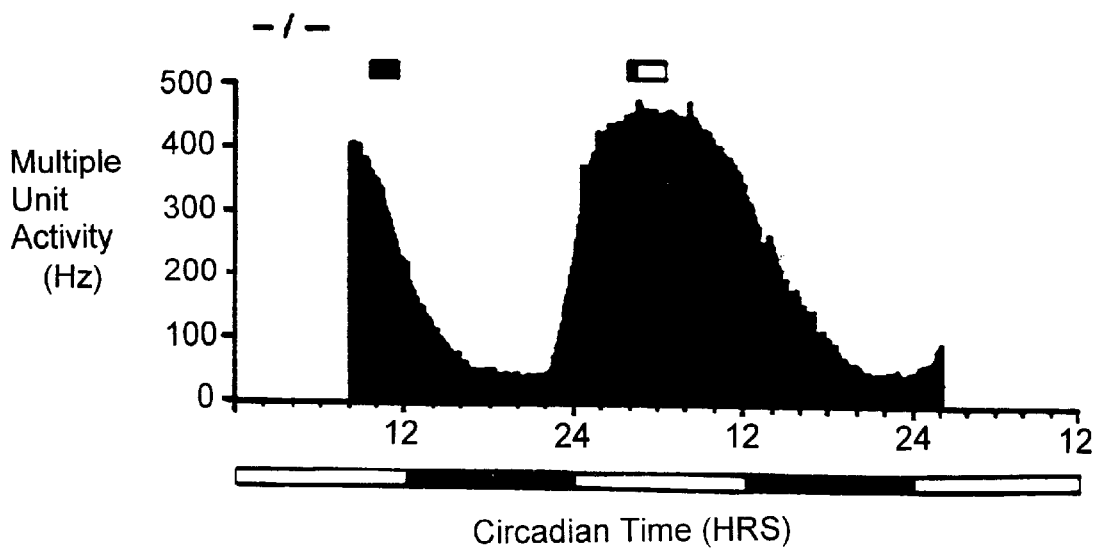

Next examined was the ability of melatonin to acutely suppress SCN neuronal firing in wild-type and $Mel_{1a}$ receptor-deficient mice. For this aspect of study, multiunit recordings of hypothalamic slices containing SCN were used. With this system, circadian rhythms in neuronal firing rate can be consistently monitored for 3 days in culture. The suppressive effect of melatonin on neuronal firing was examined at two circadian times (CT, where CT 12 is the projected time of lights off in the colony room). Studies were conducted at CT 9.5–11.5 on day 1 in culture and CT 4.5–6.5 on day 2. The results are shown in FIGS. 3A and 3B, which are a pair of graphs illustrating inhibition by melatonin of multiunit SCN activity in mice. Melatonin induced a suppression of multiunit activity from day 2 CT 4.5–6.5 in the wild-type brain slice, while no suppression occurred in the homozygous mutant slice. CT 9.5–11.5 was also examined because this is the time when melatonin has been shown to shift the phase of the circadian rhythm in locomotor activity in vivo (Benloucif, S., and Dubocovich, M. L., *J. Biol. Rhythms* 11:113–125, 1996; Cassone, V. M., *Trends Neurosci.* 13:457–464, 1990) as well as the rhythm in SCN firing rate in vitro (McArthur, A. J., et al., *Brain Res.* 565:158–161, 1991; McArthur, A. J., et al., Endocrinology 138:627–634, 1997; Starkey, S. J., et al., NeuroReport 6:1947–1951, 1995). Because of the large decline in firing rate between CT 9.5–11.5 (FIGS. 3A and 3B), the effects of melatonin application on firing rate was assessed relative to a separate group of slices to which vehicle was applied at the identical time. Melatonin effects were also examined at CT 4.5–6.5 because the peak of the rhythm in multiunit activity occurs at this time, and multiunit activity is constant over this period. Melatonin treatments at CT 4.5–6.5 were compared with prior vehicle treatments (at CT 4.0–4.5) of the same slice. Circadian rhythms of firing rate were comparable in phase and amplitude between wild-type and homozygous mutant mice (FIGS. 3A and 3B).

Figure 4A:
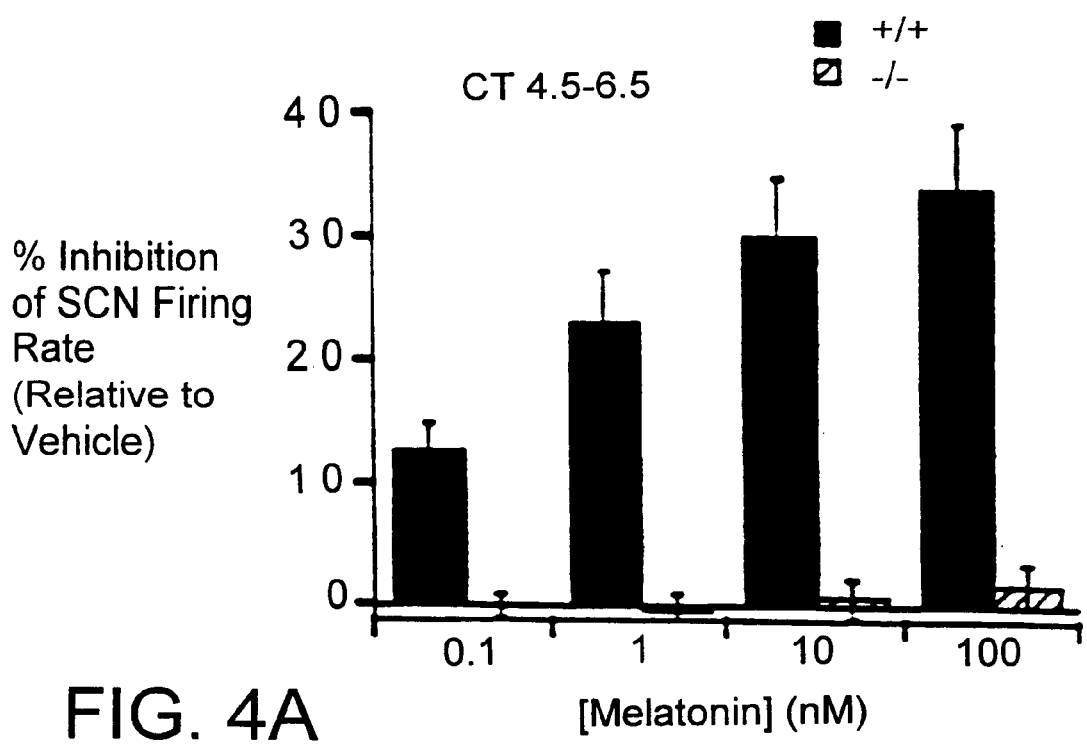
FIGS. 4A and 4B are two bar graphs illustrating the effect of the Mella receptor knockout on melatonin-induced inhibition of multiunit SCN activity. 4A illustrates effects of melatonin treatment from circadian time 4.5–6.5 (day 2 in culture) on multiunit activity in SCN slices from wild-type (+/+, black bars) and homozygous mutant (−/−, cross-hatched bars) mice. For each slice, the percent inhibition of SCN firing rate induced by melatonin was determined relative to vehicle treatment at circadian time 4.0–4.5. Melatonin treatments consisted of 30 minutes consecutive exposures to 0.1, 1, 10, and 100 nM melatonin. All SCN slices were also treated with either vehicle or melatonin on day 1 in culture. The genotype of the animals was not identified until after experiments were completed and data were analyzed. Each value is the mean±SEM of 7 to 11 slices for each genotype at each melatonin dose. 4B illustrates the effects of melatonin treatment from circadian time 9.5–11.5 on day 1 in culture. Melatonin treatments consisted of consecutive exposures, each of 30 minutes' duration, to 0.1, 1, 10, and 100 nM melatonin. Because of the large negative slope of multiunit activity at this time (see FIG. 3), the effects of melatonin application on firing rate were assessed relative to a separate group of slices for each genotype to which vehicle was applied at identical times. The genotype of the animals was not identified until after experiments were completed and data were analyzed. Each value is the mean±SEM of 7 to 11 slices for each genotype at each melatonin dose.
Figure 4B:
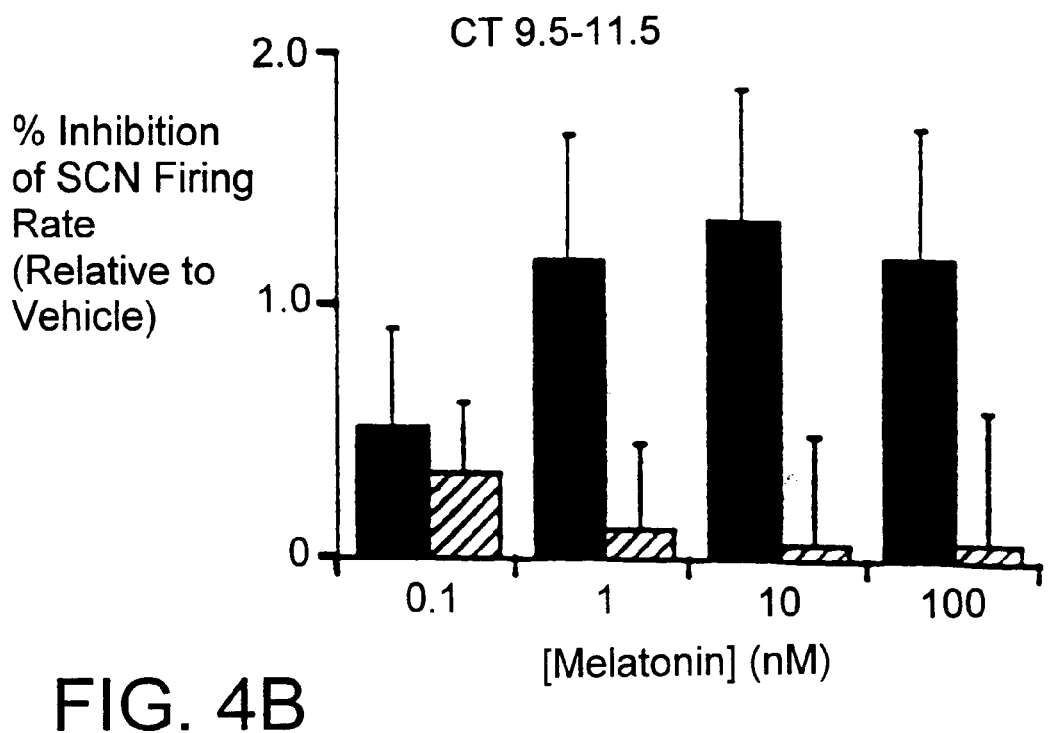

Melatonin caused a consistent inhibition of multiunit activity in SCN slices from wild-type mice. When melatonin was applied at increasing concentrations (0.1, 1, 10 and 100 nM at 30 minute intervals) from CT 4.5–6.5, there was a significant, concentration-dependent inhibition of neuronal activity in slices from wild-type mice, compared with vehicle treatment from CT 4.0–4.5 (p=0.001, one-way ANOVA; FIGS. 3A and FIG. 4A). These results are shown in FIGS. 3A and 4A. FIGS. 4A and 4B are a pair of bar graphs showing the effects of melatonin treatment from CT 4.5–6.5 on day 2 of culture (FIG. 4A) and CT 9.5–11.5 on day 1 of culture (FIG. 4B) on multiunit activity in SCN slices from wild-type and homozygous mutant mice. Percent inhibition of SCN firing rate increased steadily to over 30% with increasing melatonin concentration for CT 4.5–6.4 of day 2 (FIG. 4A), while percent inhibition increased and leveled off at about 13% for CT 9.5–11.5 of day 1 (FIG. 4B). There was no significant effect of melatonin application on day 1 in culture, relative to vehicle application, on the day 2 (CT 4.5–6.5) melatonin response data (p=0.45), so the data sets were combined. This is because there is no significant effect of melatonin treatment on day 1 to the timing of the multiunit activity peak on day 2; the broad peak of the multiunit activity rhythm precludes use of this assay for monitoring melatonin-induced phase shifts. The $EC_{50}$ of the melatonin-induced inhibition was 412 pM. When melatonin (0.1 to 100 nM) was applied from CT 9.5–11.5, there was a significant inhibition of neuronal activity compared to vehicle-treated slices (p<0.05, one-way ANOVA, FIG. 4B), but the melatonin effect was much more variable because of the steep slope of the multiunit activity pattern at this time (FIGS. 3A and 3B). These results indicate that the in vitro multiunit assay provides a reliable method for assessing the acute suppressive effect of melatonin on neuronal firing in SCN slices.

Targeted disruption of the $Mel_{1a}$ receptor abolished melatonin's ability to suppress SCN multiunit activity. At both treatment times, CT 9.5–11.5 and CT 4.5–6.5, melatonin (0.1 to 100 nM) was unable to significantly inhibit SCN multiunit activity in $Mel_{1a}$ receptor-deficient mice, relative to vehicle treatments (p>0.50 for each time, one-way ANOVAs; FIGS. 3B, 4A, and 4B). These results indicate that the $Mel_{1a}$ receptor mediates the acute inhibitory effect of melatonin observed with SCN multiunit recordings.

Studies in wild-type C57BL/6 mice showed that physiological levels of melatonin (1 nM) also inhibit SCN multiunit activity at night at CT 18 (33.9±3.9% inhibition, n=8). This is important because it is at a time when melatonin levels are normally high in vivo (Klein, D. C., in: Light and Biological Rhythms in Man. Wetterberg, L., ed., Pergamon Press, New York, pp. 55–71, 1993). Thus, melatonin can elicit its inhibitory effect on SCN function at a physiologically relevant time.

The phase shifting effects of melatonin in wild-type and $Mel_{1a}$ receptor-deficient mice were assessed using an in vitro assay in which single-unit extracellular activity is monitored from SCN slices. This in vitro method was used because it is not subject to the artifactual results sometimes observed with in vivo drug treatments (Hastings, M. H., et al., Brain Res. 591:20–26, 1992; Van Reeth, O., and Turek, F. W., Nature 339:49–51, 1989). In addition, the melatonin-induced shifts in vitro are much larger than those produced in vivo to single or multiple injections of melatonin (Cassone, V. M., Trends Neurosci. 13:457–464, 1990; McArthur, A. J., et al., Brain Res. 565:158–161, 1991; Starkey, S. J., Neurosci. Lett. 211:199–202, 1996). Moreover, studies in rats have shown that the phase-shifting effect of melatonin on the single-unit activity rhythm is a high-affinity response ($EC_{50}$<100 pM) and that it is blocked by pertussis toxin (Starkey, S. J., et al., NeuroReport 6:1947–1951, 1995; McArthur, A. J., et al., Endocrinology 138:627–634, 1997). These characteristics are consistent with melatonin's inducing phase shifts by a high-affinity, G protein-coupled melatonin receptor.

Figure 5A:
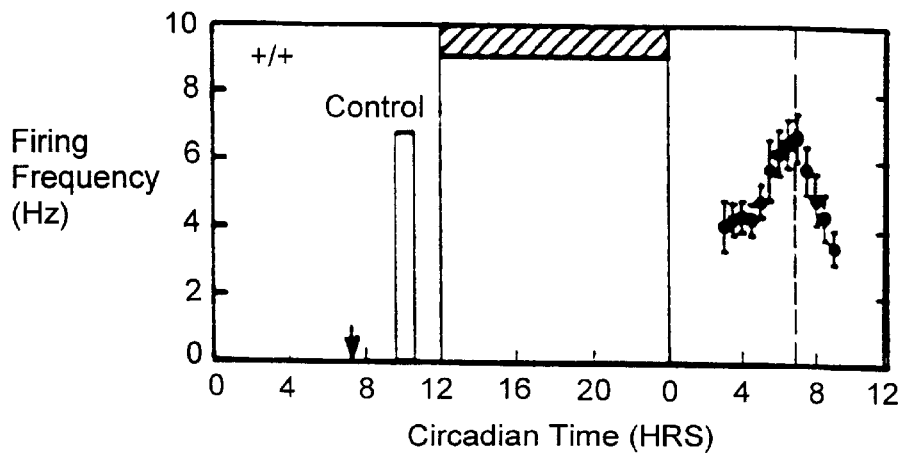
FIGS. 5A, 5B, and 5C are a series of three plots illustrating melatonin-induced phase shifts in the SCN circadian clock in mice with a targeted disruption of the Melia receptor. Electrical activity rhythms are displayed in the plot in the far right panel in each
Figure 5B:
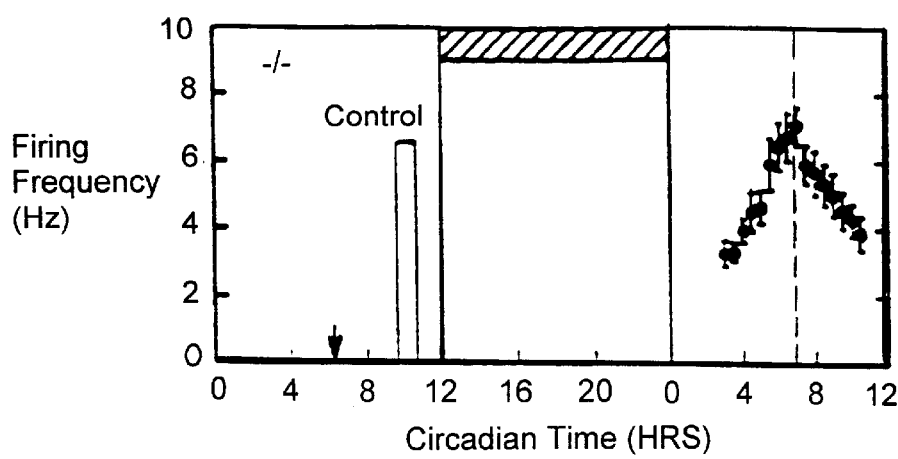
Figure 5C:
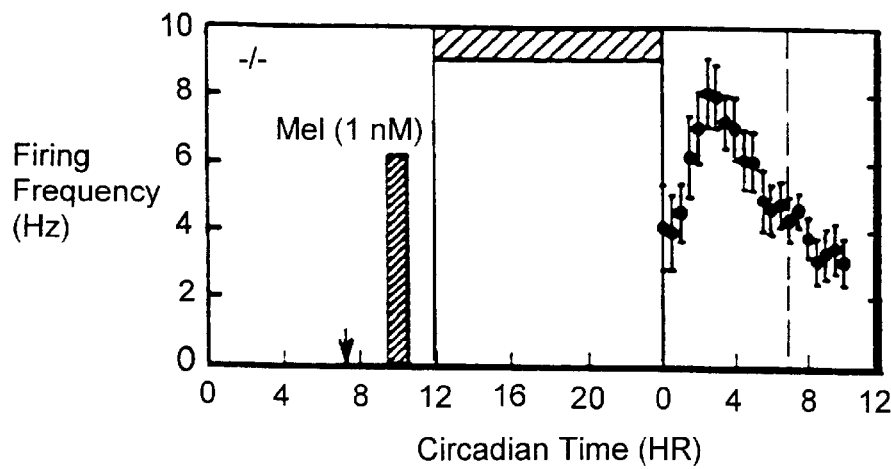
Figure 6A:
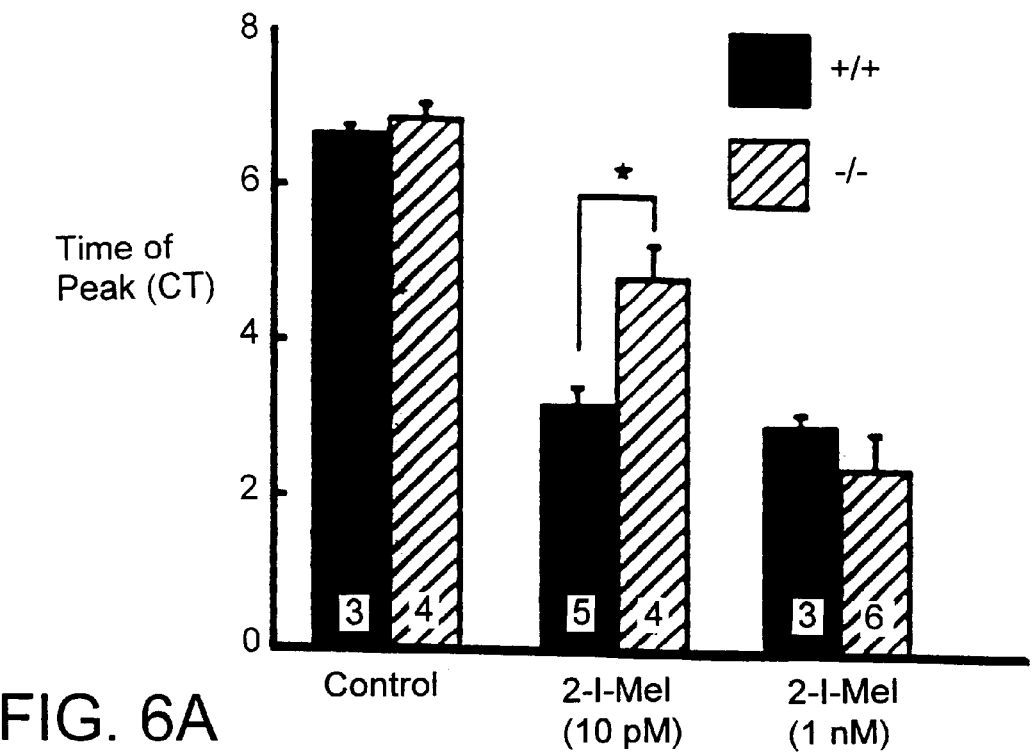
FIGS. 6A and 6B are bar charts illustrating the effect of melatonin agonist 2-iodomelatonin (2-I-Mel) in phase shifting the SCN circadian clock in mice with targeted disruption of the $Mel_{1a}$ receptor. 6A illustrates the phase-shifting effect of 10 pM or 1 nM 2-iodomelatonin on the SCN electrical activity rhythm in wild-type (+/+, black bars) and homozygous mutant (−/−, cross-hatched bars) mice. SCN slices were treated with either vehicle (control) or 2-iodomelatonin from circadian time 9.5–10.5, and the peak of the firing rate rhythm was assessed (in circadian time) on the next day. The genotype of the animals was not identified until after experiments were completed. Bars represent mean±SEM. The asterisk over the 2-I-melatonin bars is significant at p<0.01, Student's t-test. 6B illustrates the phase-shift data of 6A re-plotted to depict actual phase change (phase advance) from the control treatment. All phase shifts were significant (p<0.01, Dunnett's test).
Figure 6B:
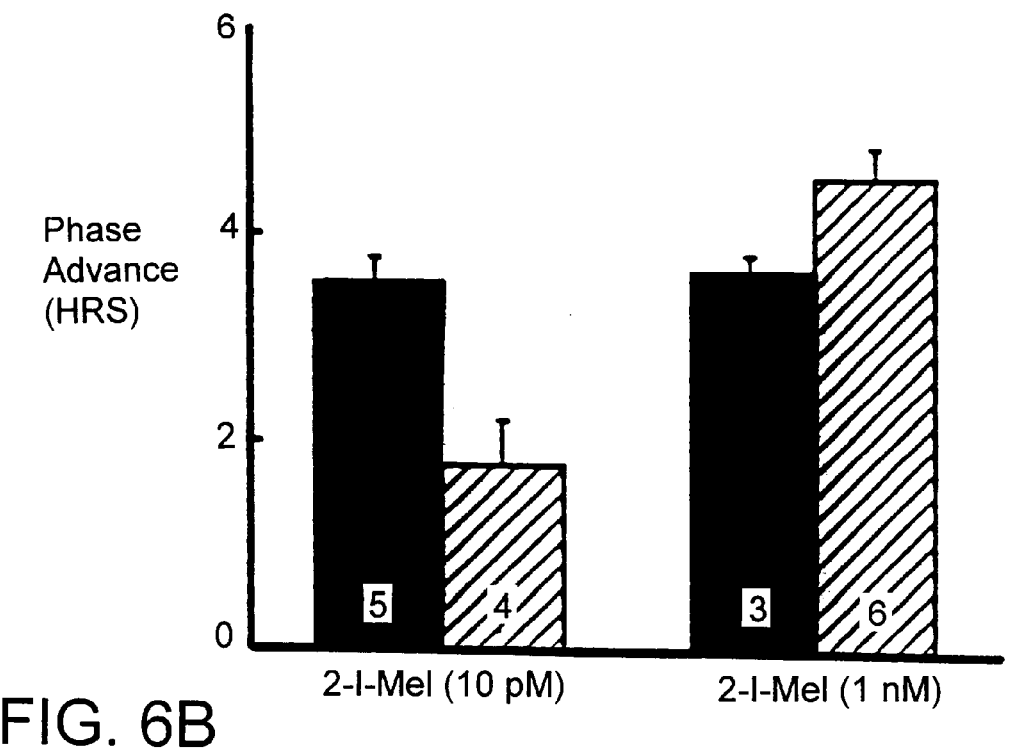

For in vitro studies, the phase shifting effect of melatonin was examined at CT 9.5–10.5 because in rats and in preliminary studies of wildtype mice, melatonin application at this time consistently elicited an approximately 4 hour phase advance in circadian phase. Also shown was that melatonin application from CT 5.5–6.5 to SCN slices from wild-type mice did not elicit significant phase shifts in the electrical activity rhythm. The CT of activity peak was 6.8±0.3 hour (n=3), compared with the control treatment (FIGS. 5A–5C). Thus, the SCN of wild-type mice exhibit a daily sensitivity to the phase shifting effects of melatonin in vitro similar to that found in rats (McArthur, A. J., et al., Endocrinology 138:627–634, 1997). Consequently, the in vitro single-unit assay is a valid method for assessing molecular mechanisms involved in melatonin-induced phase shifts in wild-type and receptor-deficient mice. It is important to note that melatonin-induced phase shifts are not apparent with the multiunit assay because of the broad firing-rate peak which occurs with multiunit recordings. For instance, no phase shift can be seen in FIGS. 3A and 3B, while it is clearly visible in FIGS. 5A–5C. Because all detectable $^{125}$I-Mel binding in SCN is abolished in $Mel_{1a}$ receptor-deficient mice, one would expect that targeted disruption of the $Mel_{1a}$ receptor would abolish the phase shifting effects of melatonin on SCN slices as monitored with the single-unit assay. However, the SCN from mice with targeted disruption of the $Mel_{1a}$ receptor still exhibited robust phase shifts to both melatonin and the melatonin agonist, 2-iodomelatonin. Melatonin (1 nM) applied from CT 9.5–10.5 to SCN slices from $Mel_{1a}$ receptor-deficient mice produced a clear, approximately 4-hour phase advance in the electrical activity rhythm peak, compared to control treatment (FIGS. 5A–5C). In addition, the phase shifting effects of 1 nM melatonin were indistinguishable between wild-type and null mutant mice (data not shown). 2-iodomelatonin at 1 nM also produced large (approximately 4 hour) phase shifts that were not significantly different in magnitude between wild-types (3.6±0.1 hour, n=3) and receptor-deficient mice (4.4±0.4 hour, n=6; p>0.05, Student's t-test). This is shown in FIGS. 6A and 6B, which are a pair of bar charts showing the phase-shifting effect of 2-iodomelatonin in mice deficient for the $Mel_{1a}$ receptor.

A lower concentration of 2-iodomelatonin was then examined to determine whether a contribution of the Melia receptor to the phase-shifting effect might be evident at a lower concentration. When 10 pM 2-iodomelatonin was applied, a clear difference in the magnitude of the phase shift was seen between wild-type and $Mel_{1a}$ receptor-deficient animals (FIGS. 6A and 6B). While 10 pM 2-iodomelatonin elicited significant phase shifts in both wild-type and $Mel_{1a}$ receptor null mutant mice (p<0.01 for each genotype vs. vehicle-treated animals; Dunnett's test), the magnitude of the phase shift in receptor-deficient mice (2.0±0.4 hours, n=4) was significantly smaller than the shift in wild-type mice (3.4±0.2 hour, n=5; p<0.01, Student's t-test). These results show that the $Mel_{1a}$ melatonin receptor is not necessary for the phase-shifting effects of melatonin on the SCN firing-rate rhythm, but the $Mel_{1a}$ subtype does contribute to the response as revealed by low 2-iodomelatonin doses.

Melatonin elicits a high-affinity phase-shift response in SCN slices from $Mel_{1a}$ receptor-deficient mice, so it is possible that melatonin-induced phase shifting in the $Mel_{1a}$ knockout mice is mediated by the other high-affinity melatonin receptor identified in mammals, the $Mel_{1b}$ melatonin receptor (Reppert, S. M., et al., Proc. Natl. Acad. Sci. USA 92:8734–8738, 1995). To further explore participation of the $Mel_{1b}$ receptor in phase-shifting activities in $Mel_{1b}$ receptor-deficient mice, the effects of pertussis toxin on melatonin-induced phase shifts were examined in these receptor-deficient mice. Pertussis toxin ADP-ribosylates the alpha subunit of $G_i$, $G_o$ and $G_q$, rendering these G proteins incapable of intracellular signaling. Because the $Mel_{1b}$ melatonin receptor signals through $G_i$, pertussis toxin should block melatonin-induced phase shifts in $Mel_{1a}$ receptor-deficient mice.

Figure 7A:
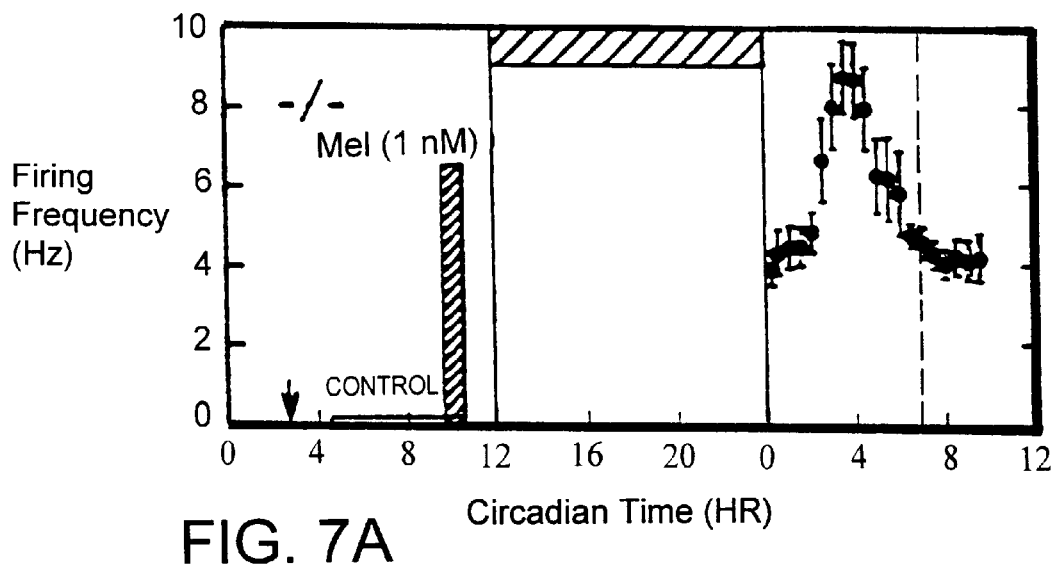
FIGS. 7A and 7B are two plots illustrating that pertussis toxin blocks melatonin-induced phase shifts in $Mel_{1a}$ receptor-deficient mice. Single-unit electrical activity rhythms in SCN slices are depicted for homozygous mutant (−/−) mice treated with 1 nM melatonin preceded by a 5-hr static preincubation with either normal medium (7A) or 1 Ag/ml pertussis toxin (7B). Data are representative of 3 studies per treatment. Arrows indicate time of slice preparation. The dark period of the light-dark cycle in the animal room is indicated by the hatched horizontal bars at the top of each panel.
Figure 7B:
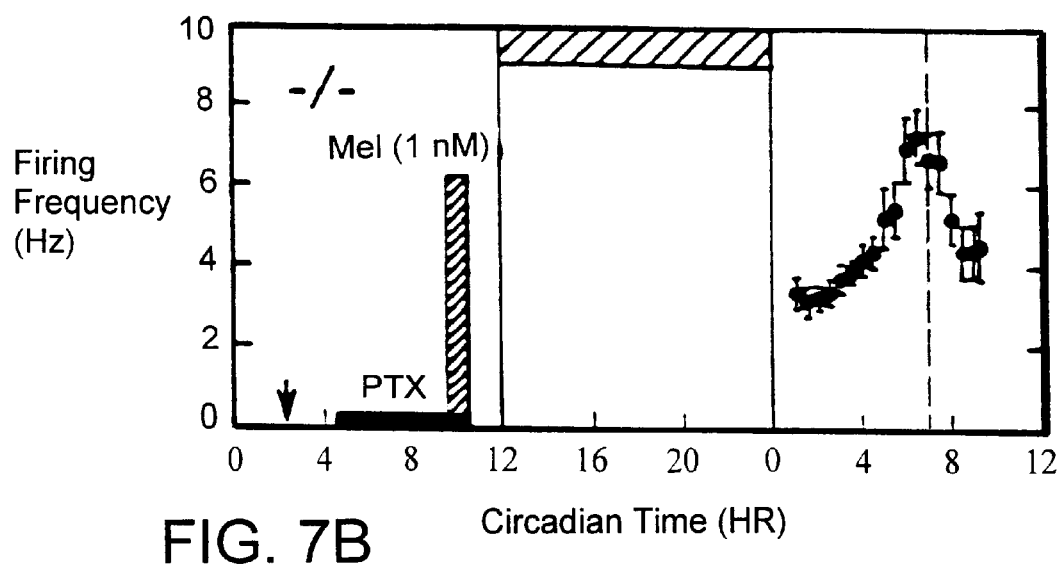
Figure 8A:
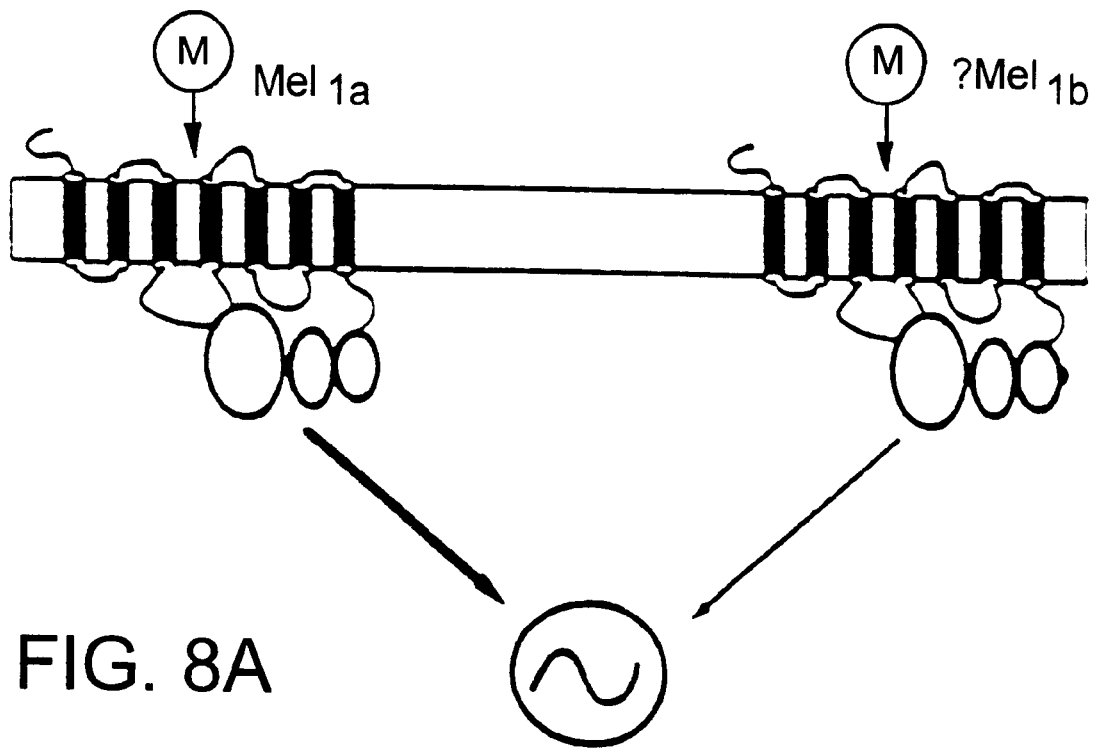
FIGS. 8A and 8B are a pair of line drawings illustrating alternative models of melatonin receptor involvement in melatonin-induced phase shifts in mouse SCN. 8A shows the $Mel_{1a}$ receptor as the primary receptor mediating melatonin phase shifts in SCN with a small contribution from the $Mel_{1b}$ receptor. 8B shows the $Mel_{1b}$ receptor as the primary receptor mediating melatonin phase shifts in SCN with a small contribution from the $Mel_{1a}$ receptor. M =melatonin.
Figure 8B:
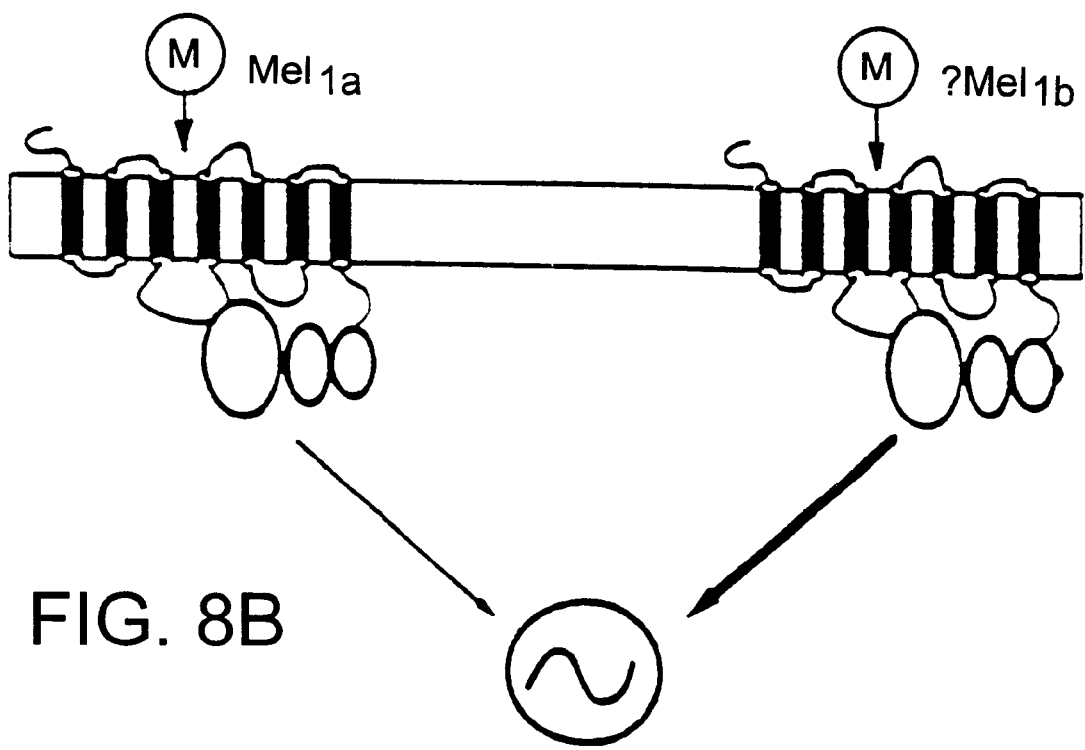

Pertussis toxin-pretreatment was found to block the ability of melatonin to phase shift the SCN electrical activity rhythm in $Mel_{1a}$ receptor-deficient mice. In SCN slices subjected to a 5-hour static bath of normal medium before treatment, 1 nM melatonin applied at CT 9.5–10.5 elicited a 3.2±0.1 hour (n=3) phase advance in circadian phase, as shown in FIG. 7A. However, when SCN slices were preincubated with pertussis toxin (1 ug/ml) for the 5 hours before the 1 nM melatonin treatment, the phase of the firing rhythm peak was not shifted. The circadian time of the activity peak was 6.6±0.1 hour, n=3, and was similar to the circadian phase of slices treated with vehicle, which exhibited a circadian time of 6.9±2 hour (FIGS. 6A and 6B). Thus, a pertussis toxin-sensitive mechanism mediates the phase-shifting effects of melatonin in $Mel_{1a}$ receptor-deficient mice.

If the $Mel_{1b}$ receptor is involved in phase-shifting activities, then it must be present in mouse SCN. Expression of the $Mel_{1b}$ receptor gene was therefore examined by RT-PCR of mRNA from punches of SCN from wild-type and $Mel_{1a}$ receptor-deficient mice. RT-PCR was used because $Mel_{1b}$ receptor transcripts in humans and rats are expressed at levels below the limits of sensitivity of standard in situ hybridization methods (Reppert, S. M., et al., *Proc. Natl. Acad. Sci. USA* 92:8734–8738, 1995). Applicants have isolated and sequenced the 2 exons of the mouse $Mel_{1b}$ receptor gene that encode the coding region (Weaver, D. R., et al., *Mol. Endocrinol.* 10: 1478–1487, 1996). This information allowed the design of primers which amplify the cDNA across the intron splice sites in the first cytoplasmic loop (Reppert, S. M., et al., *Proc. Natl. Acad. Sci. USA* 92:8734–8738, 1995).

The RT-PCR assay was performed using a modification of a previously described procedure (Kelly, J. R., et al., *Alcohol* 10:185–189, 1993). SCN were obtained from 1-week-old mice. Cylindrical punches of unilateral SCN were made from 400 μm coronal sections, using a 20-gauge needle. Total RNA was extracted from a batch of SCN punches from the same genotype (4–9 animals per batch) using an Ultraspec RNA Isolation System (Biotekx Labs, Houston, Tex.). Total RNA (approximately 2 μg) from SCN of wild-type or homozygous mutant mice was primed with random hexamers and reverse transcribed as previously described (Reppert, S. M., et al., *Neuron* 13:1177–1185, 1994). The cDNA was subjected to 25 cycles of amplification with 200 nM each of two specific primers. Amplification conditions were 94° C. for 45 seconds, 60° C. for 45 seconds and 72° C for 2 minutes. The $Mel_{1b}$ receptor-specific primers were designed to amplify cDNA across the intron splice sites in the first cytoplasmic loop. Since the intron is approximately 9 kb, amplification of the appropriate-sized cDNA fragment would eliminate amplification of genomic DNA. The $Mel_{1b}$ receptor-specific primers, which amplify a band of 367 bp, were 5'-CTC AGT GCT CAG GAA CCG CAA GCT-3' (SEQ ID NO:6) and 5'-CCT AGT ATG AGA TTT CTG GGG TGT-3' (SEQ ID NO:7). Histone-H3.3 served as a control to verify the efficiency of the RT reaction. The histone H3.3 primers, which amplify a band of 217 bp, were 5'-GCA AGA GTG CGC CCT CTA CTG-3' (SEQ ID NO:8) and 5'-GGC CTC ACT TGC CTC CTG CAA-3' (SEQ ID NO:9).

After amplification, the reaction products were subjected to electrophoresis through a 1.5% agarose gel and blotted onto GeneScreen (DuPont/New England Nuclear, Boston, Mass.). Blots were hybridized with 25-mer oligonucleotides labeled with [gamma-$^{32}$P]ATP by T4 polynucleotide kinase. For each primer pair, the oligonucleotide probes were specific for a sequence of the amplified fragment between the primers. Oligonucleotide sequences were 5'-TCA TAG TAC CAC CTA CCA CCG GGT C-3' (SEQ ID NO:10) for the Melib receptor; and 5'-CAC TGA ACT TCT GAT CCG CAA GCT C-3' (SEQ ID NO:11) for histone H3.3. Hybridizing conditions were 45° C. overnight in 0.5 M $NaPO_4$ (pH 7.2), 7% SDS, 1% BSA and 1 mM EDTA. The blots were washed twice in 0.2 M $NaPO_4$, 1% SDS and 1 mM EDTA at 45° C. for 30 minutes.

The RT-PCR results showed that the $Mel_{1b}$ receptor is expressed in the SCN of null mutant mice, yielding a band of 367 bp.

Example 2

Targeted disruption of the $Mel_{1b}$ receptor

Figure 10:
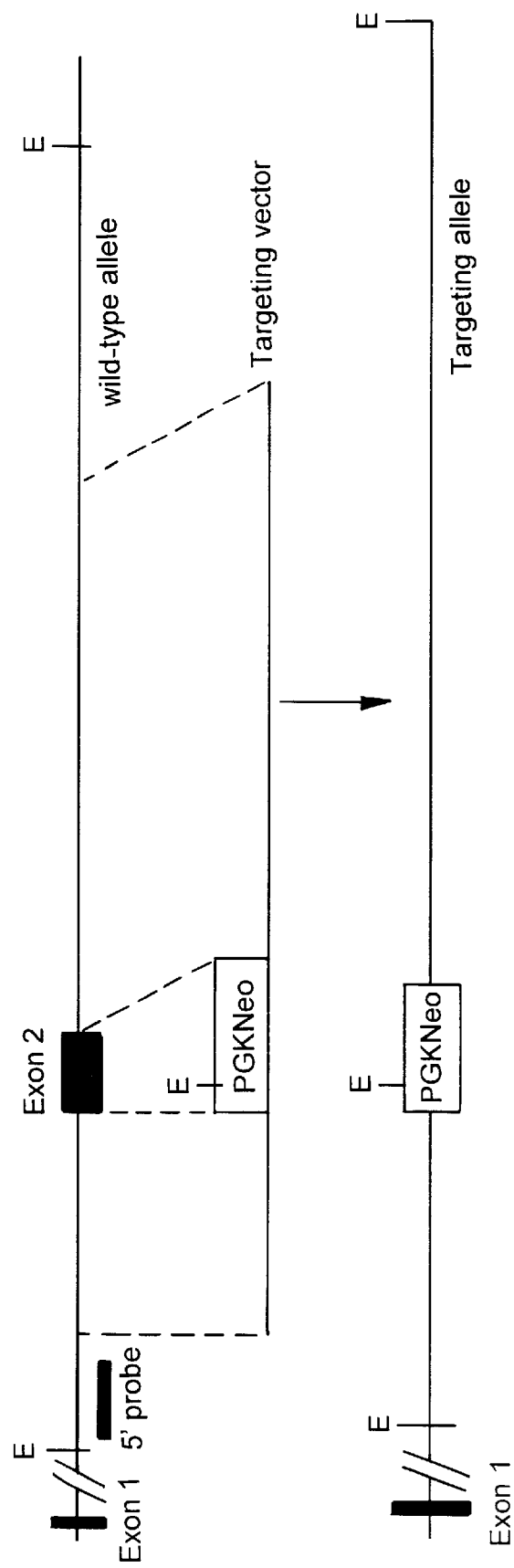
FIG. 10 is a diagram illustrating the targeted disruption of the $Mel_{1b}$ melatonin receptor gene. Exons are represented by boxes and relevant restriction sites are depicted. The center diagram shows the targeting construct in which Exon 2 has been replaced by a cassette (PGKNeo) containing a promotor-driven neomycin-resistance gene. The bottom diagram represents the targeted allele integrated into the genome by homologous recombination. E=EcoRV.

Methods analogous to the above can be used to produce mutant mice lacking the $Mel_{1b}$ receptor. The mouse $Mel_{1b}$ receptor gene (FIG. 9) is composed of two exons divided by a large (~9 kb) intron. A targeting vector was constructed from a 10 kb genomic clone which was isolated from a 129/Sv genomic library as shown in FIG. 10. FIG. 10 shows replacement of exon 2 with a cassette containing a neomycin-resistance gene under the control of the phosphoglycerate kinase-1 promotor, and about 3 kb of genomic DNA 5' of the PGKNeo cassette, and about 7 kb of genomic DNA at the 3' end. The targeting vector was transfected into 129/Sv Jl embryonic stem (ES) cells, and homologous recombination was assessed by Southern blot analysis of the EcoRV-digested DNA using a 5' probe flanking the targeted DNA (FIG. 10). Homologous recombination yields an extra band at ~5 kb in addition to the ~19 kb band also seen with the genomic DNA from the wild-type ES cells.

Clones carrying the targeted allele will be microinjected into C57BL/6 mouse blastocysts, and the resulting chimeric males mated to C57BL/6 females. Germline transmission can be tested in the offspring by Southern analysis or PCR of tail DNA from offspring with agouti coat color.

Example 3

Screening assays using $Mel_{1a}$ and $Mel_{1b}$ knockout mice

Mice lacking the various melatonin receptor subtypes can be used to test the effect of candidate compounds on circadian rhythms. Mice lacking the $Mel_{1b}$ receptor are used to test compounds that work on the $Mel_{1a}$ receptor, and vice versa. This permits isolation of a drug's effects on one receptor from its effects on the other.

$Mel_{1a}$-deficient mutant mice canbe used to identify compounds which are antagonists of melatonin specific to the $Mel_{1b}$ receptor. SCN single unit recordings are taken as described above. The SCN slices are treated with varying concentrations of melatonin (control), or the candidate compound followed by either melatonin or vehicle. The melatonin alone produces a phase shift, while treatment with vehicle alone will produce none. Treatment with a melatonin antagonist, however, followed by a melatonin treatment, should produce no phase shift. The compound then can be tested in $Mel_{1b}$ mice or wild type mice, to determine the receptor specificity of the antagonist.

Mice lacking the $Mel_{1b}$ receptor can be used to test compounds which are candidate melatonin antagonists specific for the $Mel_{1a}$ receptor. Because melatonin has the ability to suppress SCN multiunit activity, treatment of these mice with a melatonin antagonist, followed by treatment with melatonin, should result in a failure by melatonin to suppress multiunit activity. A compound which is a melatonin agonist, however, will block SCN neuronal firing as melatonin does.

Example 4

Identifying and using therapeutic agents useful for controlling biological rhythms The antagonists and agonists of melatonin that are identified with the knockout mice of the present invention may be useful as therapeutics in controlling biological rhythms in mammals. Melatonin is the primary hormone of the pineal gland, and so may possess unforeseen activities or have undesireable side effects, such as induction of reproductive tract tumors (Pierpaoli and Regelson, *Proc. Natl. Acad. Sci. USA* 91:787–791, 1994). Antagonists and agonists of melatonin, however, can be selected for both efficacy and lack of such harmful effects.

A therapeutic preparation is administered in accordance with the condition to be treated. Ordinarily, it will be administered intravenously, at a dosage, of a duration, and with the appropriate timing to elicit the desired response. Alternatively, it may be convenient to administer the therapeutic orally, nasally, or topically, e.g., as a liquid, spray, or patch. A typical dosage for a potassium channel activator is about 100 pM to 50 μM. Treatment may be repeated as necessary for alleviation of disease symptoms.

Melatonin agonists and antagonists identified with the knockout mice of the invention can be used to reentrain the endogenous melatonin rhythm of humans; treat benign prostatic hyperplasia; alleviate jet lag symptoms in humans; phase shift the sleep/wake cycle of blind people; reinforce entrainment of endogenous melatonin rhythm using low intensity light/dark cycle; control ovulation in humans or commercially important animals; control initiation or timing of puberty; and alter reproductive cycles in seasonally breeding animals. The melatonin agonists and antagonists identified with the mice of the invention can also be used to cause or prevent constriction in blood vessels and cerebral blood vessels, and to inhibit or enhance dopamine release in the retina.

Other Embodiments

It is to be understood that while the invention has been described in conjunction with the detailed description thereof, the foregoing description is intended to illustrate and not limit the scope of the invention, which is defined by the scope of the appended claims. All publications cited above are hereby incorporated by reference. Other aspects,

SEQUENCE LISTING

<160> NUMBER OF SEQ ID NOS: 12

<210> SEQ ID NO 1
<211> LENGTH: 2377
<212> TYPE: DNA
<213> ORGANISM: Mus musculus
<220> FEATURE:
<221> NAME/KEY: CDS
<222> LOCATION: (1270)...(2328)
<223> OTHER INFORMATION: intron coding sequence between positions
      1464 and 1465

<400> SEQUENCE: 1

```
cggaggatga ccttgaacct ctgatccttt gccttccctc ctgggtgctg gggttacgtg      60
actgaggtgc cacatccagt ttatacagca ctagaaatgg agtctaagat tttgcaaatg     120
ctgcacagga gccctaacga cagagccaca cgctcaggcc cctcaattct gcattgcatt     180
tcttcttgaa attattgatg aacacaacca ttttacttaa tatgatttgt tgagacagga     240
ttttatacag caacactgat tgaccacaca gctcaagatg cccccaaact ggtgttgatt     300
ctcctgcctc agcctccaga gctacgacac attgtttaat tttaatacag attttaatat     360
tgtcatgtca tgcttttctg gtattcatct tcttaaaatg tattttcttc attttcttc      420 actctttcaa agggactttg gaaatgctta ggaattggac agccataaaa tatatggaga     480
gcatgaaaat ttaagtgttc aatatgagaa catcatatgt tttgtgtaag tctccttccc     540
catgttgaag aaagtttttgg ggttttgttc cattctgtac agagctggct aatgcacttc     600
ccagaaatct tacactgtgg ttctacgtct gcttctatta tctcaagttt ctgttttcac     660
tgatagtttc aaaagaacat atacacctgt catctgcaaa tatttacatt ttgtttcgtt     720
taattgccag aaacacccag aacagacatt aaatcgtgct atgccagacg gaaagggtgt     780
gatttaatat cattattact ttatttttac acatcattga ctattaaagt tgatgagtta     840
gattctattt tcatcttcat tttccggata agacatccag ggcatctagt cctggttagg     900
```

-continued

```
attcaagttc gtgaatcgag gccttccagg gtgcaagttt ccctccactt gatgcctcca    960
cgtgtctcac cgagtctcgc cacacggggg cgcaacgtgc acgcactgtg ggacctccga   1020
gtccaagttg ctgggcagtg gacagcaggt gtcagcaggc ggcagtggcc aagtgcagag   1080 aggtgtcct accaccggga gggggctgga gtgggcagga cagccgcgaa gcaatcataa    1140
ggatgcaaag tagacgcggg agggccataa aaagtggcgg agagggctcg agcagagctg   1200
agcagttgag ggctccgggg cgacaggaca atggccctgg ctgtgctgcg gtgaggcacc   1260
```

```
cagggqacc atg aag ggc aat gtc agc gag ctg ctc aat gcc act cag cag   1311
         Met Lys Gly Asn Val Ser Glu Leu Leu Asn Ala Thr Gln Gln
          1               5                  10 gct cca ggc ggc ggg gag gga ggg aga cca cga ccg tcc tgg ctg gcc     1359
Ala Pro Gly Gly Gly Glu Gly Gly Arg Pro Arg Pro Ser Trp Leu Ala
 15              20                  25                  30 tct aca ctg gcc ttc atc ctc atc ttt acc atc gtg gtg gac att ctg     1407
Ser Thr Leu Ala Phe Ile Leu Ile Phe Thr Ile Val Val Asp Ile Leu
             35                  40                  45 ggc aac ctg ctg gtc atc ctg tct gtg tac cgc aac aag aag ctc agg     1455
Gly Asn Leu Leu Val Ile Leu Ser Val Tyr Arg Asn Lys Lys Leu Arg
         50                  55                  60 aac tca ggg aat ata ttt gtg gtg agt tta gct gtg gca gac ctc gtg     1503
Asn Ser Gly Asn Ile Phe Val Val Ser Leu Ala Val Ala Asp Leu Val
     65                  70                  75 gtg gct gtt tac cct tat ccc ttg gtg ctg aca tct atc ctt aac aac     1551
Val Ala Val Tyr Pro Tyr Pro Leu Val Leu Thr Ser Ile Leu Asn Asn
 80                  85                  90 gga tgg aat ctg gga tat cta cac tgt caa gtc agc gca ttt cta atg     1599
Gly Trp Asn Leu Gly Tyr Leu His Cys Gln Val Ser Ala Phe Leu Met
 95                 100                 105                 110 ggc ttg agt gtc atc ggc tcg ata ttc aac atc acg ggg atc gct atg     1647
Gly Leu Ser Val Ile Gly Ser Ile Phe Asn Ile Thr Gly Ile Ala Met
            115                 120                 125 aac cgt tac tgc tac att tgc cac agc ctc aag tac gac aaa ata tac     1695
Asn Arg Tyr Cys Tyr Ile Cys His Ser Leu Lys Tyr Asp Lys Ile Tyr
        130                 135                 140 agt aac aag aac tcg ctc tgc tac gtg ttc ctg ata tgg atg ctg aca     1743
Ser Asn Lys Asn Ser Leu Cys Tyr Val Phe Leu Ile Trp Met Leu Thr
        145                 150                 155 ctc atc gcc atc atg ccc aac ctg caa acc gga aca ctc cag tac gat     1791
Leu Ile Ala Ile Met Pro Asn Leu Gln Thr Gly Thr Leu Gln Tyr Asp
160                 165                 170 ccc cgg atc tac tcc tgt acc ttc acc cag tct gtc agc tca gcg tac     1839
Pro Arg Ile Tyr Ser Cys Thr Phe Thr Gln Ser Val Ser Ser Ala Tyr
175                 180                 185                 190 acg ata gca gtg gtg gtt ttc cat ttc atc gtg cct atg att att gtc     1887
Thr Ile Ala Val Val Val Phe His Phe Ile Val Pro Met Ile Ile Val
                195                 200                 205 atc ttc tgc tac tta agg ata tgg gtc ctg gtc ctt cag gtc aga cgg     1935
Ile Phe Cys Tyr Leu Arg Ile Trp Val Leu Val Leu Gln Val Arg Arg
        210                 215                 220 agg gtg aaa ccc gac aac aag ccc aaa ctg aag ccc cag gac ttc agg     1983
Arg Val Lys Pro Asp Asn Lys Pro Lys Leu Lys Pro Gln Asp Phe Arg
            225                 230                 235 aac ttt gtc acc atg ttc gta gtt ttt gta ctt ttt gcc att tgt tgg     2031
Asn Phe Val Thr Met Phe Val Val Phe Val Leu Phe Ala Ile Cys Trp
        240                 245                 250 gcc cca ctc aac ctc ata ggt ctt att gtg gcc tca gac cct gcc acc     2079
Ala Pro Leu Asn Leu Ile Gly Leu Ile Val Ala Ser Asp Pro Ala Thr
255                 260                 265                 270
```

```
atg gtc ccc agg atc cca gag tgg ctg ttc gtg gct agt tac tac ctg    2127
Met Val Pro Arg Ile Pro Glu Trp Leu Phe Val Ala Ser Tyr Tyr Leu
            275                 280                 285 gcg tac ttc aac agc tgc ctc aac gca att ata tac gga cta ctg aat    2175
Ala Tyr Phe Asn Ser Cys Leu Asn Ala Ile Ile Tyr Gly Leu Leu Asn
            290                 295                 300 cag aat ttc aga aag gaa tac aaa aag att att gtc tcg ttg tgc aca    2223
Gln Asn Phe Arg Lys Glu Tyr Lys Lys Ile Ile Val Ser Leu Cys Thr
            305                 310                 315 gcc aag atg ttc ttt gtg gag agt tca aat gaa gaa gca gat aag att    2271
Ala Lys Met Phe Phe Val Glu Ser Ser Asn Glu Glu Ala Asp Lys Ile
            320                 325                 330 aaa tgt aag ccc tct cca cta ata ccc aat aat aac tta ata aag gtg    2319
Lys Cys Lys Pro Ser Pro Leu Ile Pro Asn Asn Asn Leu Ile Lys Val
335                 340                 345                 350 gac tct gtt taaaaagcca gtggtgctag cagattatcc acactggttg            2368
Asp Ser Val gggtcttcc                                                          2377

<210> SEQ ID NO 2
<211> LENGTH: 353
<212> TYPE: PRT
<213> ORGANISM: Mus musculus

<400> SEQUENCE: 2

Met Lys Gly Asn Val Ser Glu Leu Leu Asn Ala Thr Gln Gln Ala Pro
 1               5                  10                  15

Gly Gly Gly Glu Gly Arg Pro Arg Pro Ser Trp Leu Ala Ser Thr
                20                  25                  30

Leu Ala Phe Ile Leu Ile Phe Thr Ile Val Val Asp Ile Leu Gly Asn
            35                  40                  45

Leu Leu Val Ile Leu Ser Val Tyr Arg Asn Lys Lys Leu Arg Asn Ser
        50                  55                  60

Gly Asn Ile Phe Val Val Ser Leu Ala Val Ala Asp Leu Val Val Ala
 65                  70                  75                  80

Val Tyr Pro Tyr Pro Leu Val Leu Thr Ser Ile Leu Asn Asn Gly Trp
                 85                  90                  95

Asn Leu Gly Tyr Leu His Cys Gln Val Ser Ala Phe Leu Met Gly Leu
            100                 105                 110

Ser Val Ile Gly Ser Ile Phe Asn Ile Thr Gly Ile Ala Met Asn Arg
        115                 120                 125

Tyr Cys Tyr Ile Cys His Ser Leu Lys Tyr Asp Lys Ile Tyr Ser Asn
    130                 135                 140

Lys Asn Ser Leu Cys Tyr Val Phe Leu Ile Trp Met Leu Thr Leu Ile
145                 150                 155                 160

Ala Ile Met Pro Asn Leu Gln Thr Gly Thr Leu Gln Tyr Asp Pro Arg
                165                 170                 175

Ile Tyr Ser Cys Thr Phe Thr Gln Ser Val Ser Ser Ala Tyr Thr Ile
            180                 185                 190

Ala Val Val Val Phe His Phe Ile Val Pro Met Ile Ile Val Ile Phe
        195                 200                 205

Cys Tyr Leu Arg Ile Trp Val Leu Val Leu Gln Val Arg Arg Arg Val
    210                 215                 220

Lys Pro Asp Asn Lys Pro Lys Leu Lys Pro Gln Asp Phe Arg Asn Phe
225                 230                 235                 240
```

-continued

```
Val Thr Met Phe Val Val Phe Val Leu Phe Ala Ile Cys Trp Ala Pro
                245                 250                 255
Leu Asn Leu Ile Gly Leu Ile Val Ala Ser Asp Pro Ala Thr Met Val
            260                 265                 270
Pro Arg Ile Pro Glu Trp Leu Phe Val Ala Ser Tyr Tyr Leu Ala Tyr
        275                 280                 285
Phe Asn Ser Cys Leu Asn Ala Ile Ile Tyr Gly Leu Leu Asn Gln Asn
    290                 295                 300
Phe Arg Lys Glu Tyr Lys Lys Ile Ile Val Ser Leu Cys Thr Ala Lys
305                 310                 315                 320
Met Phe Phe Val Glu Ser Ser Asn Glu Glu Ala Asp Lys Ile Lys Cys
                325                 330                 335
Lys Pro Ser Pro Leu Ile Pro Asn Asn Asn Leu Ile Lys Val Asp Ser
                340                 345                 350
Val
```

<210> SEQ ID NO 3
<211> LENGTH: 24
<212> TYPE: DNA
<213> ORGANISM: Mus musculus

<400> SEQUENCE: 3
gagtccaagt tgctgggcag tgga                                          24

<210> SEQ ID NO 4
<211> LENGTH: 26
<212> TYPE: DNA
<213> ORGANISM: Mus musculus

<400> SEQUENCE: 4
gaagttttct cagtgtcccg caatgg                                        26

<210> SEQ ID NO 5
<211> LENGTH: 27
<212> TYPE: DNA
<213> ORGANISM: Mus musculus

<400> SEQUENCE: 5
ccagctcatt cctccactca tgatcta                                       27

<210> SEQ ID NO 6
<211> LENGTH: 24
<212> TYPE: DNA
<213> ORGANISM: Mus musculus

<400> SEQUENCE: 6
ctcagtgctc aggaaccgca agct                                          24

<210> SEQ ID NO 7
<211> LENGTH: 24
<212> TYPE: DNA
<213> ORGANISM: Mus musculus

<400> SEQUENCE: 7
cctagtatga gatttctggg gtgt                                          24

<210> SEQ ID NO 8
<211> LENGTH: 21
<212> TYPE: DNA
<213> ORGANISM: Mus musculus

```
<400> SEQUENCE: 8
gcaagagtgc gccctctact g                                           21

<210> SEQ ID NO 9
<211> LENGTH: 21
<212> TYPE: DNA
<213> ORGANISM: Mus musculus

<400> SEQUENCE: 9
ggcctcactt gcctcctgca a                                           21

<210> SEQ ID NO 10
<211> LENGTH: 25
<212> TYPE: DNA
<213> ORGANISM: Mus musculus

<400> SEQUENCE: 10
tcatagtacc acctaccacc gggtc                                       25

<210> SEQ ID NO 11
<211> LENGTH: 25
<212> TYPE: DNA
<213> ORGANISM: Mus musculus

<400> SEQUENCE: 11
cactgaactt ctgatccgca agctc                                       25

<210> SEQ ID NO 12
<211> LENGTH: 1095
<212> TYPE: DNA
<213> ORGANISM: Mus musculus

<400> SEQUENCE: 12
atgcctgaga acagctcaat ccctaactgc tgtgaggcca gcgggctggc agcgcgccct    60
agttggtctg ggtcagccgg agccaggcca cctgtgactg cccgggcccc ctgggtggct   120
cccatgctat ctacagtagt cgtcgtcacc acagccgtgg acttcgtggg gaacctgctt   180
gtctcctctc agtgctcagg aaccgcaagc tgcggaacgc aggtaatttg tttgtggttg   240
agtctggcct tggctgactt ggtgatagcc ttgtaccctt acccactgat ccttgtggcc   300
attatccgtg acggttgggt ccttggggag ccccactgca aggccagtgc ctttgtgatg   360
ggcctgagtg tcattggctc tgtcttcaac atcacagcca ttgccatcaa ccgctactgc   420
tgcatctgtc atagtaccac ctaccaccgg gtctgcagtc actggtatac tcccatctac   480
atcagcctcg tctggctcct cactctggtg ctttggtgc ccaatttctt tgtggggtct   540
ttagagtatg atccacgcat ctattcctgc accttcatcc agacagccag cacacagtac   600
acggcagctg tggtggccat ccacttcctc cttcccatgg ctgtggtgtc cttctgctac   660
ctgcgaatct gggtactggt gctccaggcc cgaaggaagg ccaaggctac gaggaagctg   720
cgtctgagac cgagtgattt gcgcagtttc ctaaccatgt ttgcagtgtt tgtggttttt   780
gccatatgct gggcccccct caactgtatc ggccttgcag tggccatcaa cccagaggca   840
atggctctcc aggtcccaga agggctcttt gtcaccagtt acttcttagc ttactttaac   900
agctgcctta tgccattgt ttatgggctc ctgaaccaga acttccgcag ggagtacaag   960
aggatccttt tggccatatg gaacactagg cgctgcatac agcatgcttc caaacactgt  1020
```

```
                                          -continued cttactgagg agcgacaggg cccgacgcca cctgctgcca gggctaccgt gcctgtcaag    1080
gaaggtgctc tctag                                                    1095
``` advantages, and modifications are withih the scope of the following claims.

What is claimed is:

1. A transgenic mouse whose genome comprises a disruption in an endogenous melatonin 1a receptor genes wherein said disruption results in decreased expreission or a lack of expression of said endogenou, melatonin 1a receptor gene, thereby causing a decrease in high affinity binding of melatonin in the hypothalamic suprachiasmatic nuclei and hypophyseal pars tuberalis of said mouse.

2. The mouse of claim 1, wherein said mouse is homozygous for the disrupted melatonin 1a receptor gene.

3. The mouse of claim 1, wherein said disruption results in a null mutation.

4. a nauronal cell line decended from a cell of the mouse of claim 1, wherein the disruption in the endogenous melatonin 1a receptor gene results in decreased expression or a lack of expression of said endogenous melatonin 1a receptor gene, therby causing a decrease in high afinity binding of melatonin.

5. The neuronal cell line of claim 4, wherein the cell line is descended from a cell of the mouse of claim 2.

6. The neuronal cell line of claim 4, wherein the cell line is descended from a cell of the mouse of claim 3.

7. A method of determining whether a candidate compound is a potential melatonin 1b receptor antagonist, said method comprising:
   a) adminiering melatonin to the suprachiasmatic nuclei of the mouse of claim 1 in the presence of the candidate compound; and
   b) measuring the phase shift in neuronal firing of said suprachiasmatic nuclei, wherein a decrease in phase shift in the presence of both melatomin and the candidate compound, relative to that seen in the presence of melatonin but the absence of the candidate compound, is an indication that the candidate compound is a potential melatonin 1b receptor antagonist.

8. A method of determining whether a candidate compound affects neuronal firing in the suprachiasmatic nuclei other than via the melatonin 1a receptor, said method comprising:
   a) administering a candidate compound to the suprachiasmatic nuclei of the mouse of claim 1; and
   b) measuring the phase shift in neuronal firing of said suprachiasmatic nuclei, wherein an effect on phase shift in the presence of the candidate compound is an indication that the candidate compound exerts an effect on neuronal firing in the suprachiasmatic other than via the melatonin 1a receptor.

9. A method of determining whether a candidate compound potentially affects neuronal firing the suprachiasmatic nuclei via the melatonin 1a receptor, said method comprising:
   a) administering a candidate compound to the suprachiasmatic nuclei of a transgenic mouse whose genome comprises a homozygous disruption in the endogenous melatonin 1b receptor gene; and
   b) measuring the phase shift in neuronal firing of said suprachiasmatic nuclei, wherein a decrease in suprachiasmatic nuclei neuronal firing in the presence of the candidate compound, relative to that seen in the absence of the candidate compound, is an indication that the candidate compound potentially exerts an effect via the melatonin 1a receptor.

10. A method of determining whether a candidate compound is a potential melatonin 1a receptor antagonist, said method comprising:
    a) administering melatonin to the suprachiasmatic nuclei of a tansgenic mouse whose genome comprises a homozygous disruption in the endogenous melatofin 1b receptor gene in the presence of the candidate compound; and
    b) measuring the phase shift in neuronal firing of said suprachiasmatic nuclei, wherein an increase in suprachiasmatic nuclei neuronal firing in the presence of the candidate compound, relative to tbat seen in melatonin-treated suprachiasmatic nuclei in the absence of the compound, is an indication that the candidate compound is a potential melatonin 1a recetor antagonist.

11. A neuronal cell line descended from a neuronal cell whose genome comprises a disruption in an endogenous melatonin 1a receptor gene, wherein said disruption results in decreased expression or a lack of expression of said endogenous melatonin 1a receptor gene, thereby causing a decrease in high affinity binding of melatonin.

* * * * *

UNITED STATES PATENT AND TRADEMARK OFFICE
CERTIFICATE OF CORRECTION

PATENT NO.   : 6,326,526 B1
DATED        : December 4, 2001
INVENTOR(S)  : Steven M. Reppert et al.

It is certified that error appears in the above-identified patent and that said Letters Patent is hereby corrected as shown below:

Column 1,
Line 41, delete "," after "124", insert -- I --

Column 4,
Lines 25 and 54, delete "mella", insert -- $Mel_{1a}$ --
Line 56, delete "FIG", insert -- figure --

Column 5,
Line 29, delete "Ag", insert -- $\mu$g --
Line 45, delete "CDNA", insert -- cDNA --

Column 6,
Line 16, delete "melia", insert -- $mel_{1a}$ --
Line 54, start new paragraph after "Genotyping by Southern Blot Analysis"
Line 63, delete "Genotyoing", insert -- Genotyping --

Column 7,
Line 7, after FIG. 2. move "$^{125}$I-Mel in vitro Autoradiography" move to line 8; do not indent (title of next section)
Line 43, delete "1", insert -- I --

Column 9,
Line 37, delete "MRNA", insert -- mRNA --
Line 40, delete "branding", insert -- binding --
Line 50, delete "amoderate", insert -- moderate --
Line 64, delete "5"

Column 12,
Line 42, delete "Melia", insert -- $Mel_{1a}$ --

UNITED STATES PATENT AND TRADEMARK OFFICE
CERTIFICATE OF CORRECTION

PATENT NO. : 6,326,526 B1
DATED : December 4, 2001
INVENTOR(S) : Steven M. Reppert et al.

It is certified that error appears in the above-identified patent and that said Letters Patent is hereby corrected as shown below:

Column 14,
Line 10, delete "Melib", insert -- $Mel_{1b}$ --

Column 26,
Line 6, delete "melatofin", insert -- melatonin --
Line 12, delete "tbat", insert -- that --

Signed and Sealed this

Fifteenth Day of October, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,326,526 B1
DATED : December 4, 2001
INVENTOR(S) : Steven M. Reppert et al.

It is certified that error appears in the above-identified patent and that said Letters Patent is hereby corrected as shown below:

Title page,
Item [56], References Cited, PUBLICATIONS, insert -- Reppert, S.M. Journal of Biological Rhythms 12(6):528-531.* --
"Kelley et al.," delete "PRC", insert -- PCR --
"Mason et al.," delete "putatuve", insert -- putative --
"McArthur et al." (1st occurrence), after "reset", insert -- s the rat --
"Nelson et al.," delete "recptors", insert -- receptors --
"Van Reeth et al.," delete "of", insert -- or --

Column 25,
Line 13, delete "genes", insert -- gene --
Line 14, delete "experission", insert -- expression --
Line 15, delete "endogenou", insert -- endogenous --
Line 23, delete "a nauronal", insert -- A neuronal --
Line 27, delete "afinity", insert -- affinity --
Line 36, delete "adminiering", insert -- administering --
Line 41, delete "melatomin", insert -- melatonin --

Signed and Sealed this

Twenty-seventh Day of May, 2003

JAMES E. ROGAN
*Director of the United States Patent and Trademark Office*